(12) United States Patent
El-Difrawy

(10) Patent No.: US 12,168,800 B2
(45) Date of Patent: *Dec. 17, 2024

(54) METHODS AND SYSTEMS FOR EVALUATING MICROSATELLITE INSTABILITY STATUS

(71) Applicant: LIFE TECHNOLOGIES CORPORATION, Carlsbad, CA (US)

(72) Inventor: Sameh El-Difrawy, Santa Clarita, CA (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/529,188

(22) Filed: Dec. 5, 2023

(65) Prior Publication Data

US 2024/0175084 A1 May 30, 2024

Related U.S. Application Data

(63) Continuation of application No. 18/152,813, filed on Jan. 11, 2023, now Pat. No. 11,866,778, which is a
(Continued)

(51) Int. Cl.
*G16B 40/20* (2019.01)
*C12Q 1/6809* (2018.01)
(Continued)

(52) U.S. Cl.
CPC ......... *C12Q 1/6869* (2013.01); *C12Q 1/6809* (2013.01); *C12Q 1/6886* (2013.01);
(Continued)

(58) Field of Classification Search
CPC ......... G16B 20/20; G16B 40/20; G16B 50/00
See application file for complete search history.

(56) References Cited

U.S. PATENT DOCUMENTS 7,058,517 B1 * 6/2006 Denton ................. G16B 50/30
702/19
10,400,014 B2 * 9/2019 Howorka ............. C07K 14/245
(Continued)

OTHER PUBLICATIONS

Chalmers, Z.R. et al., "Analysis of 100,000 Human Cancer Genomes Reveals the Landscape of Tumor Mutational Burden", Genome Medicine, vol. 9, No. 1, Apr. 19, 2017, pp. 1-14, XP055510901.
(Continued)

*Primary Examiner* — Eliyah S. Harper
(74) *Attorney, Agent, or Firm* — Carolyn Koenig

(57) ABSTRACT

Methods for evaluating microsatellite instability (MSI) analyze nucleic acid sequence reads corresponding to a plurality of marker regions for MSI. The marker regions may include long homopolymers and/or short tandem repeats (STRs). For a target homopolymer, a histogram of homopolymer signal values is calculated based on flow space signal measurements for the homopolymer region in the sequence reads. A score per marker based on features of the histogram of homopolymer signal values is determined for each marker region corresponding to the target homopolymers. For a target STR, the method includes calculating a histogram of repeat lengths for sequence reads corresponding to the marker region of the target STR. A score per STR marker is calculated based on features of the histogram of repeat lengths. A plurality of per marker scores may be combined to form a total MSI score for the sample.

20 Claims, 23 Drawing Sheets

Specification includes a Sequence Listing.

Related U.S. Application Data continuation of application No. 16/595,681, filed on Oct. 8, 2019, now Pat. No. 11,572,586.

(60) Provisional application No. 62/858,387, filed on Jun. 7, 2019, provisional application No. 62/785,596, filed on Dec. 27, 2018, provisional application No. 62/745,161, filed on Oct. 12, 2018.

(51) Int. Cl.
| | | |
|---|---|---|
| *C12Q 1/6869* | (2018.01) | |
| *C12Q 1/6886* | (2018.01) | |
| *G16B 20/00* | (2019.01) | |
| *G16B 50/00* | (2019.01) | |

(52) U.S. Cl.
CPC ............ *G16B 20/00* (2019.02); *G16B 40/20* (2019.02); *G16B 50/00* (2019.02); *C12Q 2600/156* (2013.01)

(56) References Cited

U.S. PATENT DOCUMENTS

| | | | | |
|---|---|---|---|---|
| 2003/0138418 | A1* | 7/2003 | Eishingdrelo | C07K 14/705 435/325 |
| 2009/0311786 | A1* | 12/2009 | Fire | C12N 15/11 435/375 |
| 2011/0171634 | A1* | 7/2011 | Xiao | C12Q 1/6825 530/391.1 |
| 2012/0096583 | A1* | 4/2012 | Azhakanandam | G16B 20/20 800/278 |
| 2015/0337388 | A1 | 11/2015 | Garner, Jr. et al. | |
| 2016/0340722 | A1* | 11/2016 | Platt | G16B 20/20 |
| 2017/0073663 | A1* | 3/2017 | Wang | C12N 15/90 |
| 2017/0114107 | A1* | 4/2017 | Meuser | C12N 1/12 |
| 2017/0151282 | A1* | 6/2017 | Discher | A61K 49/0041 |
| 2017/0175189 | A1* | 6/2017 | Hensel | G16B 20/20 |
| 2017/0212983 | A1* | 7/2017 | Cai | C12Q 1/6841 |
| 2018/0117171 | A1* | 5/2018 | Mooney | A61K 47/554 |
| 2018/0181707 | A1* | 6/2018 | El-Difrawy | C12Q 1/6869 |
| 2018/0237863 | A1* | 8/2018 | Namsaraev | C12Q 1/701 |
| 2019/0323037 | A1* | 10/2019 | Buerckstuemmer | A61K 35/545 |
| 2020/0115744 | A1* | 4/2020 | El-Difrawy | G16B 20/20 |
| 2020/0352978 | A1* | 11/2020 | Van Battum | C12N 15/113 |
| 2020/0390786 | A1* | 12/2020 | Garraway | A61K 39/39533 |
| 2020/0397821 | A1* | 12/2020 | Frost | C07K 14/7155 |

OTHER PUBLICATIONS

Kautto, E.A. et al., "Performance Evaluation for Rapid Detection of Pan-Cancer Microsatellite Instability with MANTIS", Oncotarget, vol. 8, No. 5, Dec. 12, 2016, pp. 7452-7463, XP055651336.

Pankov, A et al., "Abstract 2267: A Novel Method for Classification of Microsatellite Instability (MSI) Using the Oncomine Tumor Mutation Load assay", Proceedings of the American Association for Cancer Research Annual Meeting 2018, Apr. 14-18, 2018, Cancer Research, vol. 78, No. 13, Suppl., Jul. 2018, pp. 1-4, XP055651269.

PCT/US2019/055110, Search Report and Written Opinion, Dec. 18, 2019.

Redford, L. et al., "A Novel Panel of Short Mononucleotide Repeats Linked to Informative Polymorphisms Enabling Effective High Volume Low Cost Discrimination between Mismatch Repair Deficient and Proficient Tumours", PLOS ONE, vol. 13, No. 8, Aug. 29, 2018, p. e0283052, XP055651331.

Zhu, L. et al., "A Novel and Reliable Method to Detect Microsatellite Instability in Colorectal Cancer by Next-Generation Sequencing", The Journal of Molecular Diagnostics, vol. 28, No. 2, Mar. 2018, pp. 225-231, XP055651393.

\* cited by examiner

| MSI Marker | CRC Tumor | Endo Tumor | Gastric Tumor | Endo Normal | CRC Normal | Endo Normal | Gastric Normal |
|---|---|---|---|---|---|---|---|
| BAT25 | 1.88 | 1.52 | 0 | 0 | 0.41 | 0 | 0 |
| BAT26 | 1.15 | 1.64 | 1.51 | 0.86 | 0.01 | 0 | 0 |
| NR21 | 3.29 | 2.11 | 1.37 | 0.19 | 0.04 | 0.05 | 0.12 |
| NR24 | 2.74 | 2.15 | 0.79 | 0 | 0.22 | 0.09 | 0.33 |
| NR_22 | 2.11 | 2.87 | 1.22 | 0.1 | 0.36 | 0.28 | 0.01 |
| MSIM_1 | 1.15 | 0.92 | 2.41 | 0 | 0.18 | 0.15 | 0.12 |
|  | ⋮ | ⋮ | ⋮ | ⋮ | ⋮ | ⋮ | ⋮ |
| LIMCH1 | 0.48 | 0.11 | 0.58 | 0.08 | 0.08 | 0.04 | 0.04 |
| PRMD2 | 0.45 | 0.78 | 0.23 | 0 | 0.02 | 0.12 | 0.07 |
| RNF43 | 1.94 | 0.14 | 0.11 | 0.09 | 0.08 | 0.2 | 0.07 |
| MSI Score | 125.33 | 97.92 | 128.53 | 0.86 | 6.37 | 0 | 1.26 |

FIG. 9

| SAMPLE | NR21 | BAT26 | BAT25 | NR24 | MONO27 | MSI |
|---|---|---|---|---|---|---|
| GC-2 | + | + | + | + | + | High |
| GC-5 | | | | | | Stable |
| EC-2 | + | | + | + | + | High |
| EC-4 | | | | | | Stable |
| EC-5 | | + | + | | | High |

FIG. 10

| SAMPLE | NGS Result | MSI Score |
|---|---|---|
| Gastric Cancer Tumor - GC-2 | MSI-H | 81.56 |
| Gastric Cancer Tumor - GC-5 | Normal | 5.38 |
| Endometrial Cancer Tumor - EC-2 | MSI-H | 85.71 |
| Endometrial Cancer Tumor - EC-4 | Normal | 16.09 |
| Endometrial Cancer Tumor - EC-5 | MSI, a few markers fire | 27.83 |

FIG. 11

| | | | | |
|---|---|---|---|---|
| hg19 | PRIMER | LEFT FLANK CATT | 18 HP'S | AAT RIGHT FLANK | 3' PRIMER |
| SCC 1 | PRIMER | LEFT FLANK GATG | 18 HP'S | TAC RIGHT FLANK | 3' PRIMER |
| SCC 2 | PRIMER | LEFT FLANK GAT | 14 HP'S | CGT RIGHT FLANK | 3' PRIMER |
| SCC 3 | PRIMER | LEFT FLANK TGA | 22 HP'S | GCG RIGHT FLANK | 3' PRIMER |

FIG. 20

METHODS AND SYSTEMS FOR EVALUATING MICROSATELLITE INSTABILITY STATUS

CROSS-REFERENCE

This application is a continuation of U.S. application Ser. No. 18/152,813 filed Jan. 11, 2023, which is a continuation of U.S. application Ser. No. 16/595,681 filed Oct. 8, 2019, now U.S. Pat. No. 11,572,586, which claims the benefit under 35 U.S.C. § 119(e) of U.S. Application No. 62/858,387 filed Jun. 7, 2019, U.S. Application No. 62/785,596 filed Dec. 27, 2018, and U.S. Application No. 62/745,161 filed Oct. 12, 2018. The entire contents of the aforementioned applications are incorporated by reference herein.

SEQUENCE LISTING

The instant application contains a Sequence Listing which has been submitted electronically in XML format and is hereby incorporated by reference in its entirety. Said XML copy, created on Jan. 10, 2024, is named TP103553USCON2_SL.xml and is 4,122 bytes in size.

FIELD

This application generally relates to methods, systems, computer-readable media, compositions, and kits for detection of microsatellite instability (MSI), and, more specifically, to methods, systems, computer-readable media, compositions, and kits for detection of MSI based on or using nucleic acid sequencing data and next-generation sequencing technology or systems in conjunction with primers for detection of one or more MSI events of interest.

SUMMARY

Cancer-associated instabilities at microsatellite locations throughout the genome have been shown to be predictive of response to immunotherapy treatment. A Microsatellite Instability High (MSI-H) status can result when the DNA Mismatch Repair (MMR) system fails to work probably and is associated with hypermutability of short DNA sequence repeats, microsatellite locations, throughout the genome. In 1997, NCI recommended utilizing a panel of five MSI markers for detecting colorectal cancer (CRC). The traditional approach uses capillary electrophoresis (CE) and utilizes the difference in marker profile among a tumor/normal tissue pair to determine the MSI Status of that tumor.

Recently, there has been a growing demand to develop more sensitive solutions to MSI detection with a larger number of markers. Next Generation Sequencing (NGS) provides a natural solution for that demand with the ability to process multiple samples and a large number of markers. MSI markers can be very long homopolymers, dinucleotide (di-nuc) and trinucleotide (tri-nuc) short tandem repeats (STRs). These types of motifs are not easily amplified or sequenced accurately due to the existence of different artifacts including stutter.

There is a need for new and improved methods, systems, computer-readable media, compositions, and kits for better and more accurate detection of MSI, including better and more accurate detection of genomic regions for MSI status evaluation. There is a need for accurately evaluating MSI status based on different types of MSI markers, such as for long homopolymers and STRs. There is a need for determining MSI status using tumor only samples.

According to an exemplary embodiment, there is provided a method for detecting microsatellite instability (MSI) in a sample, including: (1) receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions; (2) for each of the sequence reads, aligning at least a portion the left flank sequence with a reference left flank, wherein the reference left flank borders a reference repeat region of a reference nucleic acid sequence corresponding to the particular marker region; (3) for the repeat region corresponding to a target homopolymer in the sequence reads, calculating a histogram of homopolymer signal values based on flow space signal measurements for the target homopolymer, wherein at least a portion of the marker regions corresponds to target homopolymers; (4) determining a score per marker based on features of the histogram of homopolymer signal values for each marker region corresponding to the target homopolymers to produce a plurality of scores; and (5) combining the plurality of scores to form a total MSI score for the sample.

According to an exemplary embodiment, there is provided computer-readable media comprising machine-readable instructions that, when loaded in a machine-readable memory and executed by the processor, are configured to cause a system to perform a method detecting microsatellite instability (MSI) in a sample, the method including: (1) receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions; (2) for each of the sequence reads, aligning at least a portion the left flank sequence with a reference left flank, wherein the reference left flank borders a reference repeat region of a reference nucleic acid sequence corresponding to the particular marker region; (3) for the repeat region corresponding to a target homopolymer, calculating a histogram of homopolymer signal values based on flow space signal measurements for the target homopolymer, wherein at least a portion of the marker regions corresponds to target homopolymers; (4) determining a score per marker based on features of the histogram of homopolymer signal values for each marker region corresponding to the target homopolymers to produce a plurality of scores; and (5) combining the plurality of scores to form a total MSI score for the sample.

According to an exemplary embodiment, there is provided a system for detecting microsatellite instability (MSI), including a machine-readable memory and a processor configured to execute machine-readable instructions, which, when executed by the processor, cause the system to perform a method for detecting MSI in a sample, the method including: 1) receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions; (2) for each of the sequence reads, aligning at least a portion the left flank sequence with a reference left flank, wherein the reference left flank borders a reference repeat region of a reference nucleic acid sequence corresponding to the particular marker region; (3) for the repeat region corresponding to a target homopolymer in the sequence reads, calculating a histogram of homopolymer signal values based on flow space signal measurements for the target homopolymer, wherein at least a portion of the marker regions corresponds to target homopolymers; (4) determining a score per marker based on features of the histogram of homopolymer signal values for each marker region corresponding to the target homopolymers to produce a plurality of scores; and (5) combining the plurality of scores to form a total MSI score for the sample.

BRIEF DESCRIPTION OF THE DRAWINGS

The novel features of the invention are set forth with particularity in the appended claims. A better understanding of the features and advantages of the embodiments will be obtained by reference to the following detailed description that sets forth illustrative embodiments, and the accompanying drawings of which:

FIG. 9 gives an exemplary table of results of per marker scores and total MSI scores for several markers in six samples with known MSI status.

FIG. 10 gives an exemplary table of results of testing of MSI status using capillary electrophoresis (CE).

FIG. 11 gives an exemplary table of results of testing of MSI status using the total MSI score determined by the NGS methods described herein.

FIG. 20 gives examples of synthetic calibration control sequences and a reference sequence from hg19.

DETAILED DESCRIPTION

Figure 1:
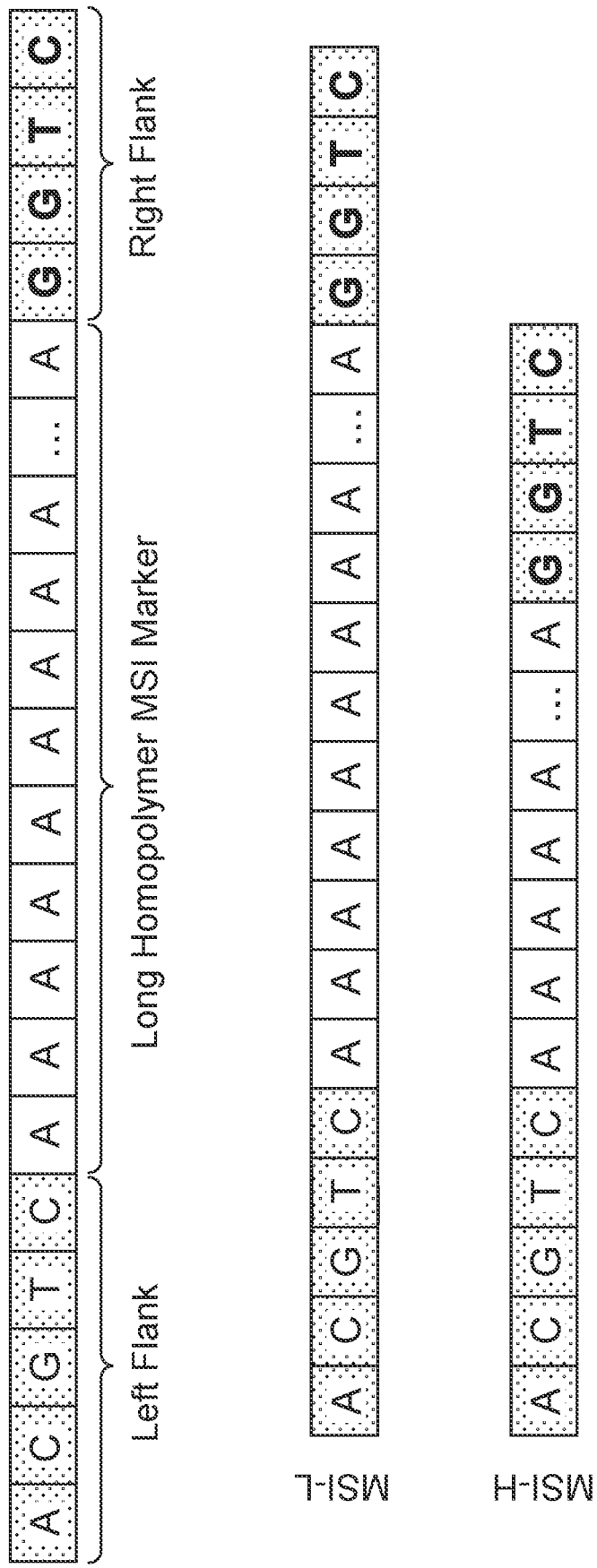
FIG. 1 illustrates examples of nucleic acid sequences having MSI marker regions and flank regions. Figure discloses SEQ ID NOS 1, 1, and 2, respectively, in order of appearance.

In accordance with the teachings and principles embodied in this application, new methods, systems and non-transitory machine-readable storage medium are provided to evaluate MSI status based on different types of MSI markers, such as for long homopolymers and STRs. Further teachings provide for determining MSI status using tumor only samples. In some embodiments, the methods described herein may allow for tens to hundreds of MSI markers to be evaluated. Primers may be targeted to amplify MSI marker regions of interest. MSI marker regions may include repeat regions, such as long homopolymers and other short tandem repeats (STRs).

In some embodiments, MSI marker regions having longer repeat regions are more sensitive to MSI than shorter ones. In some embodiments, markers with a smaller repeat unit in the repeat region are more sensitive to MSI than markers with longer repeat units. An observed behavior in long homopolymers for MSI-H samples is a shorter homopolymer length than for normal samples or a mix of shorter lengths and normal lengths in the sequence reads.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The term "allele" as used herein refers to a genetic variation associated with a gene or a segment of DNA, i.e., one of two or more alternate forms of a DNA sequence occupying the same locus.

The term "locus" as used herein refers to a specific position on a chromosome or a nucleic acid molecule. Alleles of a locus are located at identical sites on homologous chromosomes.

As used herein, the terms "adapter" or "adapter and its complements" and their derivatives, refers to any linear oligonucleotide which can be ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

As used herein, "DNA barcode" or "DNA tagging sequence" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode or DNA tagging sequence can be incorporated into the nucleotide sequence of an adapter.

In some embodiments, the disclosure provides for amplification of multiple target-specific sequences from a population of target nucleic acid molecules. In some embodiments, the method comprises hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the digesting includes partial digesting of one or more of the target-specific primers from the amplified target sequence. In some embodiments, the amplified target sequences can be ligated to one or more adapters. In some embodiments, adapters can include one or more DNA barcodes or tagging sequences. In some embodiments, amplified target sequences once ligated to an adapter can undergo a nick translation reaction and/or further amplification to generate a library of adapter-ligated amplified target sequences.

In some embodiments, the methods of the disclosure include selectively amplifying target sequences in a sample containing a plurality of nucleic acid molecules and ligating the amplified target sequences to at least one adapter and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

A plurality of defined spaces or reaction confinement regions may be arranged in an array, and each defined space or reaction confinement regions may be in electrical communication with at least one sensor to allow detection or measurement of one or more detectable or measurable parameter or characteristics. This array is referred to herein as a sensor array. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal.

In various embodiments, the phrase "base space" refers to a representation of the sequence of nucleotides. The phrase "flow space" refers to a representation of the incorporation event or non-incorporation event for a particular nucleotide flow. For example, flow space can be a series of values representing a nucleotide incorporation event (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event; however, any other symbol or designation could be used alternatively to represent and/or identify these events and non-events. In particular, when multiple nucleotides are incorporated at a given position, such as for a homopolymer stretch, the value can be proportional to the number of nucleotide incorporation events and thus the length of the homopolymer stretch.

FIG. 1 illustrates examples of nucleic acid sequences having MSI marker regions and flank regions. The MSI marker for this example is a long homopolymer as shown in the top sequence. A left flank and right flank are adjacent to the long homopolymer. A long homopolymer may have a length of 8 or more bases, for example. The flanks may include 14-15 bases, for example. The homopolymer region in the center sequence has the same length as that of a control, or reference, sequence and can be an example of MSI-Low (MSI-L) status. MSI-Low status is also referred to herein as microsatellite stable (MSS) and MSS/Normal. The bottom sequence has a much shorter homopolymer region and can be an example of MSI-H status. Shorter homopolymer length can be an indicator of MSI-H status.

Figure 2:
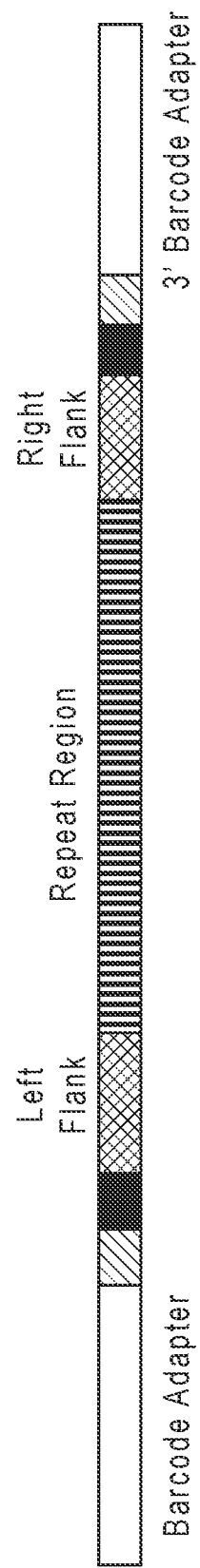
FIG. 2 illustrates an example of a sequence read having an STR region.

FIG. 2 illustrates an example of a sequence read having an STR region. The sequence read includes an STR region surrounded by a left flank and a right flank. The STR region may include repeats of a short sequence of bases, or repeat sequence. The repeat sequence may have 2 bases (dinucleotides), 3 bases (trinucleotides) or more bases. The STR region is adjacent to a non-repetitive sequence of bases of the left flank and a non-repetitive sequence of bases of the right flank. The left flank is adjacent to the 5' barcode adapter and the right flank is adjacent to the 3' barcode adapter.

In some embodiments, an aligned BAM file including aligned sequence read information is provided to a processor for analyzing the aligned sequence reads corresponding to marker regions for determining an MSI score for the sample. The sequence read may include a sequence of bases of a left flank, a sequence of bases of a right flank and a repeat region of bases positioned between a rightmost base of the left flank and a leftmost base of the right flank. The repeat region includes repeats of a single base for a homopolymer or a repeated sequence of bases for an STR. In some embodiments, portions of the aligned sequence reads may correspond to marker regions for long homopolymers and/or STRs. In some embodiments, the left and, optionally, the right flank sequence may be identified by alignment to a reference sequence using a Smith Waterman alignment algorithm or other suitable mapping algorithm. The identification of the repeat sequence and flank regions for use with the present teachings may include one or more features described in U.S. Pat. Appl. Publ. No. 2018/0181707, published Jun. 28, 2018, incorporated by reference herein in its entirety.

Figure 3:
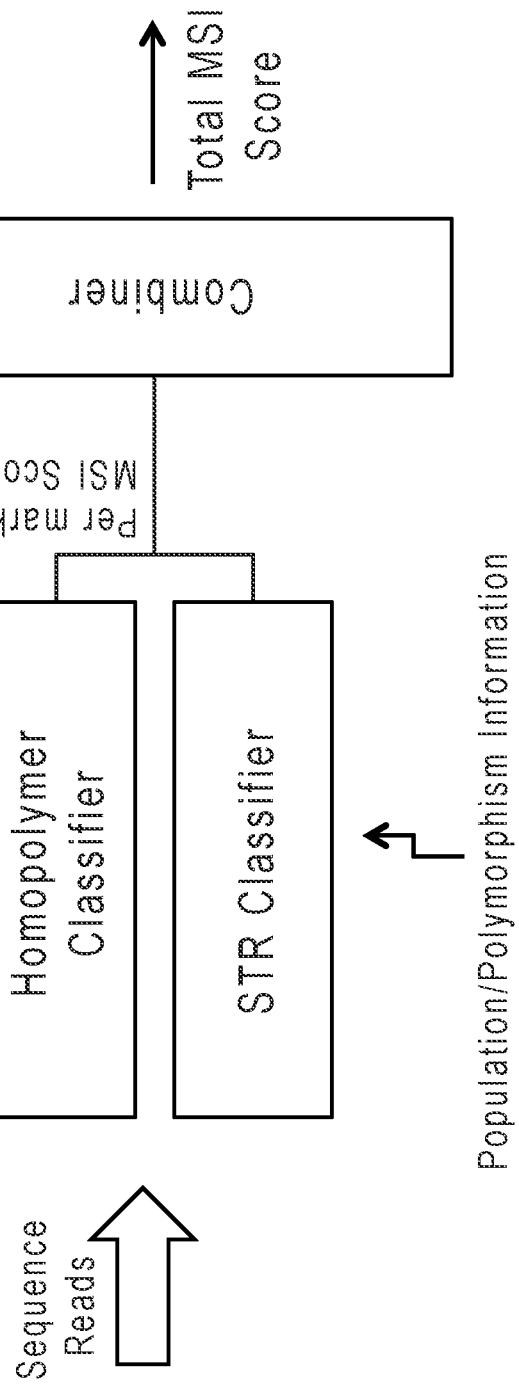
FIG. 3 is a block diagram of a method of determining an MSI score, according to an exemplary embodiment.

FIG. 3 is a block diagram of a method of determining an MSI score for a sample, according to an exemplary embodiment. The homopolymer classifier analyzes flow space signal measurements of the sequence reads corresponding to marker regions having long homopolymers to produce per marker scores for the long homopolymers. The STR classifier analyzes aligned sequence reads corresponding to marker regions having STR sequences to produce per marker scores for the STR sequences. The combiner adds per marker scores that meet threshold and coverage criteria to produce a total MSI score for the sample.

In some embodiments, a flow space signal measurement represents a signal amplitude or intensity measured in response to an incorporation or non-incorporation of a flowed nucleotide by sample nucleic acids in microwells of a sensor array. For an incorporation event, the signal amplitudes depend on the number of bases incorporated at one flow. For homopolymers, the signal amplitudes increase with increasing homopolymer length. Flow space signal measurements are described in more detail below.

In some embodiments, the homopolymer classifier determines a score per marker for the aligned sequence reads corresponding to a marker region having a long homopolymer by the following steps:

A.1. Identify sequence reads having the left flank sequence for the target homopolymer corresponding to the marker.

A.2. For each sequence read, calculate a sum of M flow space signal measurements corresponding to M nucleotide flows of the sequence of flows having the same nucleotide type as the target homopolymer to form a homopolymer (HP) signal value for the sequence read.

A.3. Calculate a histogram of HP signal values for the sequence reads in the forward direction and a histogram of HP signal values for the sequence reads in the reverse direction.

A.4. Identify features of the HP signal histograms for the forward and reverse directions to be used for evaluating the MSI status corresponding to the marker.

A.5. Calculate a score per marker using the features of the HP signal histograms.

Figure 4:
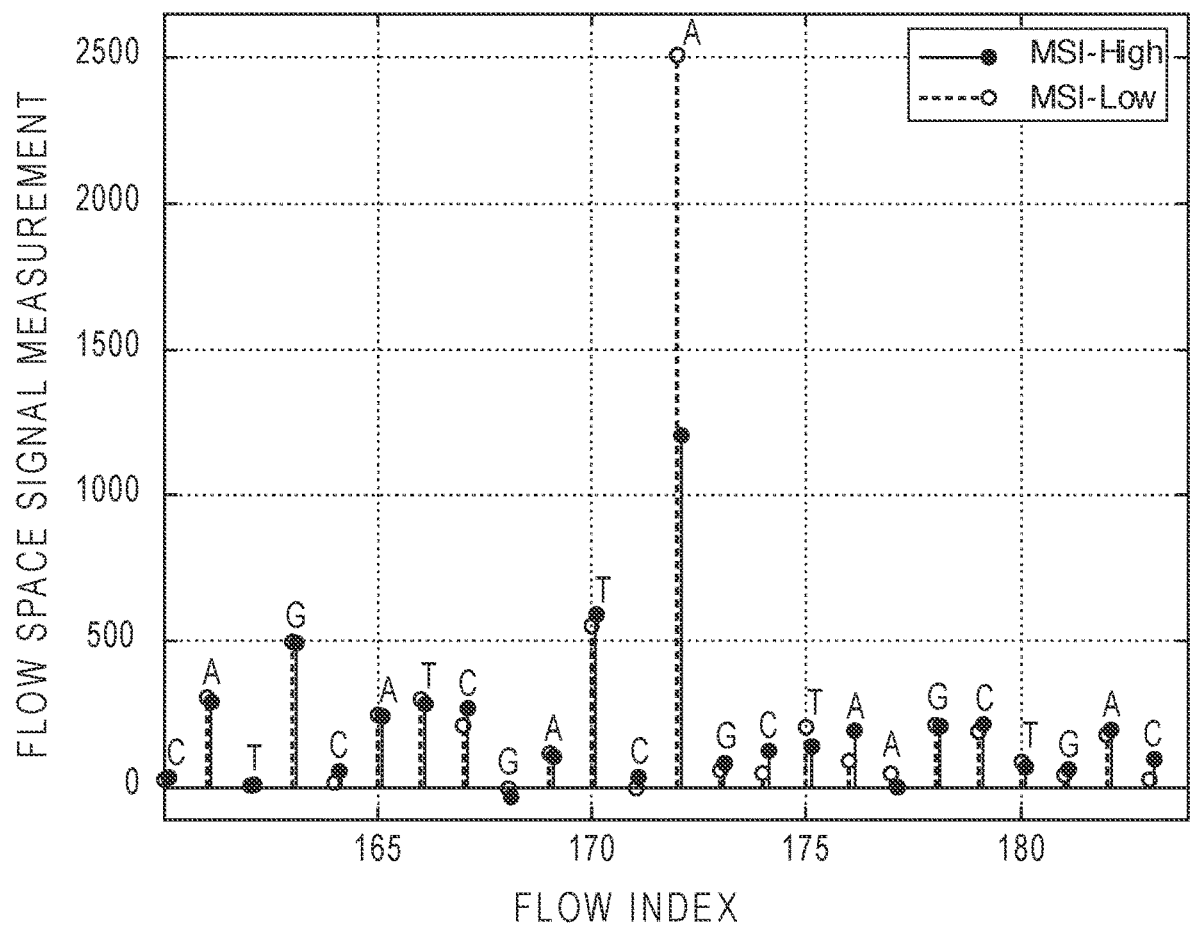
FIG. 4 shows an example of superimposed flow space signal measurements for two homopolymer sequence reads that are MSI-H and MSI-L, respectively.

FIG. 4 shows an example of superimposed flow space signal measurements for homopolymer sequence reads that are MSI-H and MSI-L, respectively. The MSI-L sequence read contains a longer homopolymer of the base A than that of MSI-H sequence read. The flow space signal measurement for the longer homopolymer has greater amplitude because more A's are incorporated in response to the nucleotide flow. The flow space signal measurement for the MSI-H sequence read has lower amplitude because the homopolymer is shorter and therefore fewer A's are incorporated in response to the nucleotide flow. The flow space signal measurements to the left of the homopolymer A indicate nucleotide incorporations for the left flank sequence (AGGATCTT). The flow space signal measurements to the right of the homopolymer A indicate nucleotide incorporations for the right flank sequence (TGCTGCAT).

In some embodiments, a number of flow space signals measurements M to be added may be determined for step A.2. For sequencing by synthesis, the sequence of flows may comprise repeats of a flow order of nucleotides, such as T-A-C-G, for example. During sequencing of a homopolymer region, multiple incorporations of a particular nucleotide may occur over several repeats of the flow order. For example, the nucleotide A may be incorporated over several repeats of the flow order when sequencing a long homopolymer. The flow space signal measurement values for the incorporations of A may decrease over subsequent repeats until the end of the homopolymer is reached and incorporations of different nucleotides begin for the flank region. The number of flow space signal measurements M corresponding to the homopolymer region may be determined by at least one of the following:

A.a) Determine the flow space signal measurements corresponding to the same nucleotide in the flow order having values above a threshold signal level. Flow space signal measurement values may decrease over subsequent flows of the same nucleotide in subsequent repeats of the flow order.

A.b) Determine the flow space signal measurements where one or more nucleotides corresponding to the flank sequence is/are incorporated. The first nucleotide corresponding to the flank sequence will be different from that of the homopolymer region.

In some embodiments, the number of flow space signal measurements in step A.a) may indicate M. In some embodiments, applying steps A.a) and A.b) may determine M based on the number flow space signal measurements for the homopolymer before the beginning of the flank sequence.

Figure 5A:
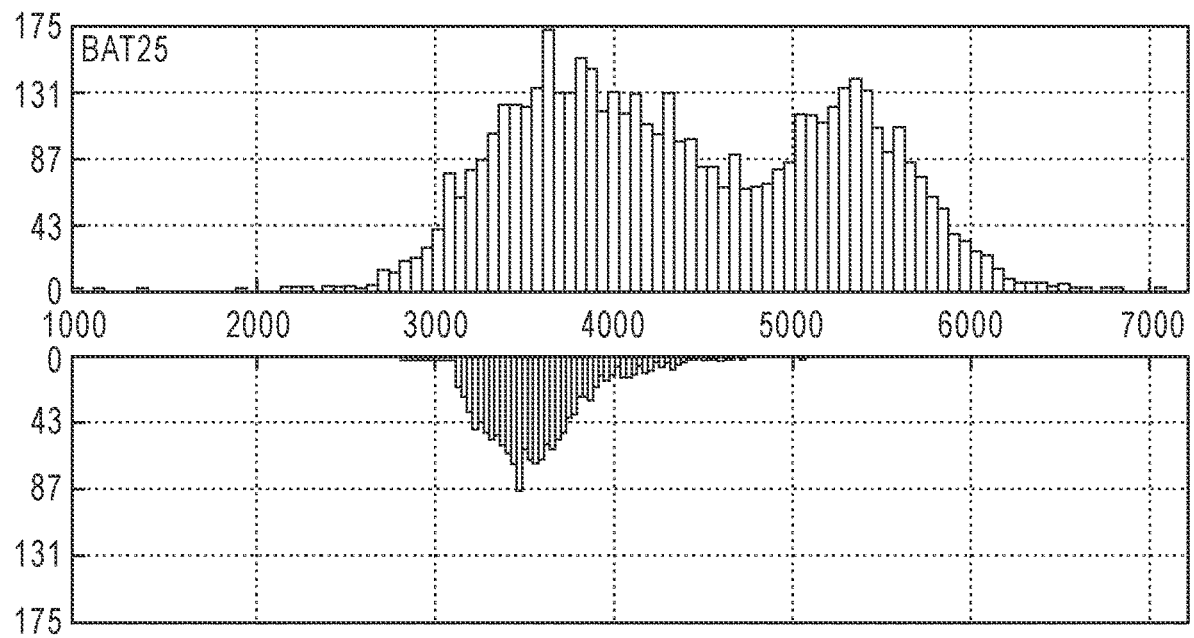
FIGS. 5A-5D show examples of histograms of HP signal values for tumor and normal samples.
Figure 5B:
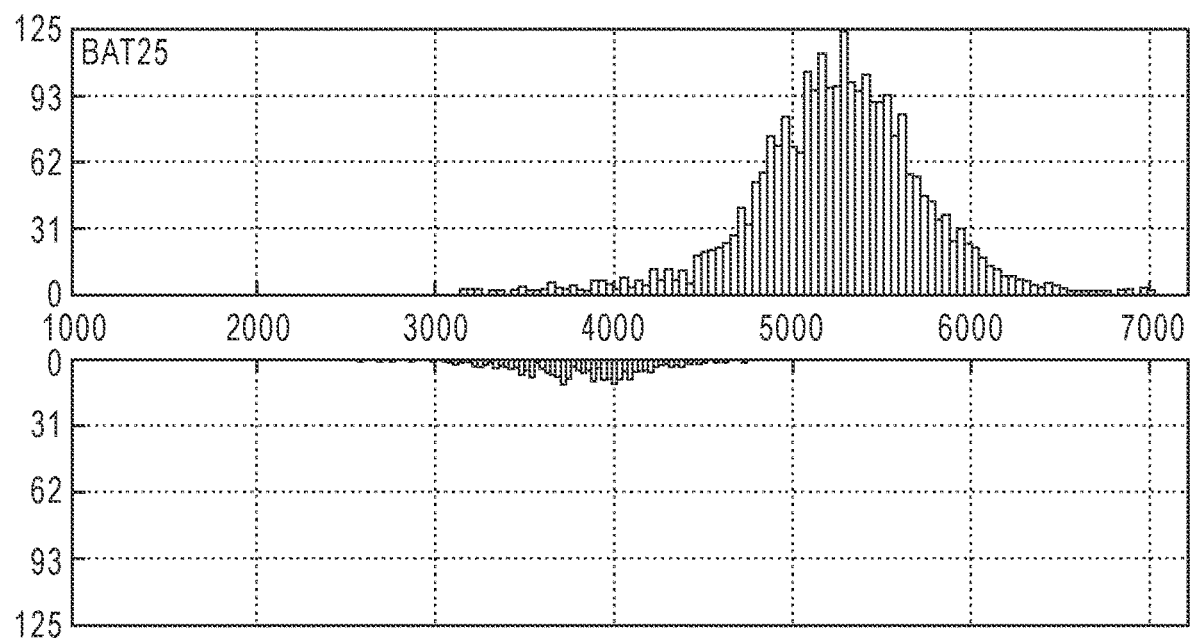
Figure 5C:
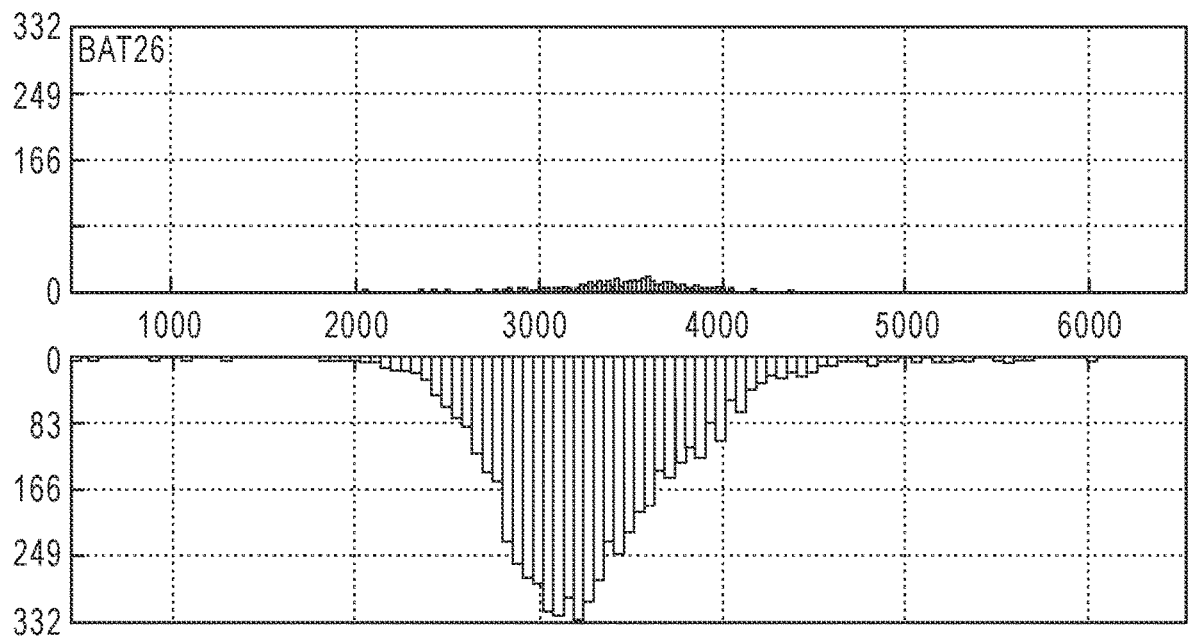
Figure 5D:
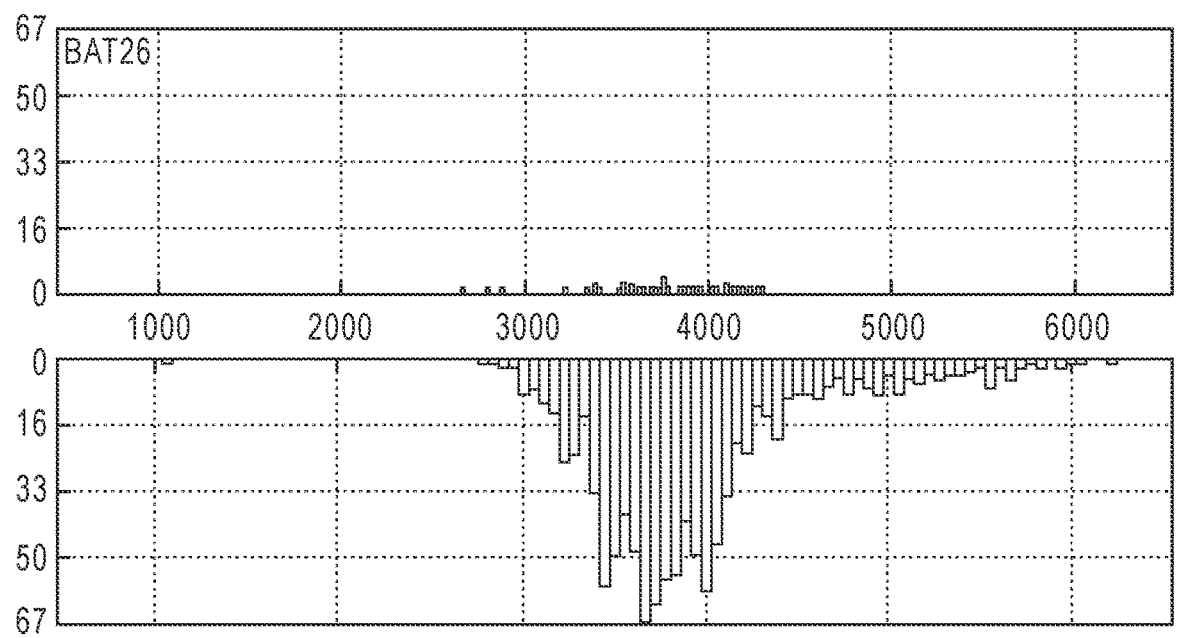
Figure 6A:
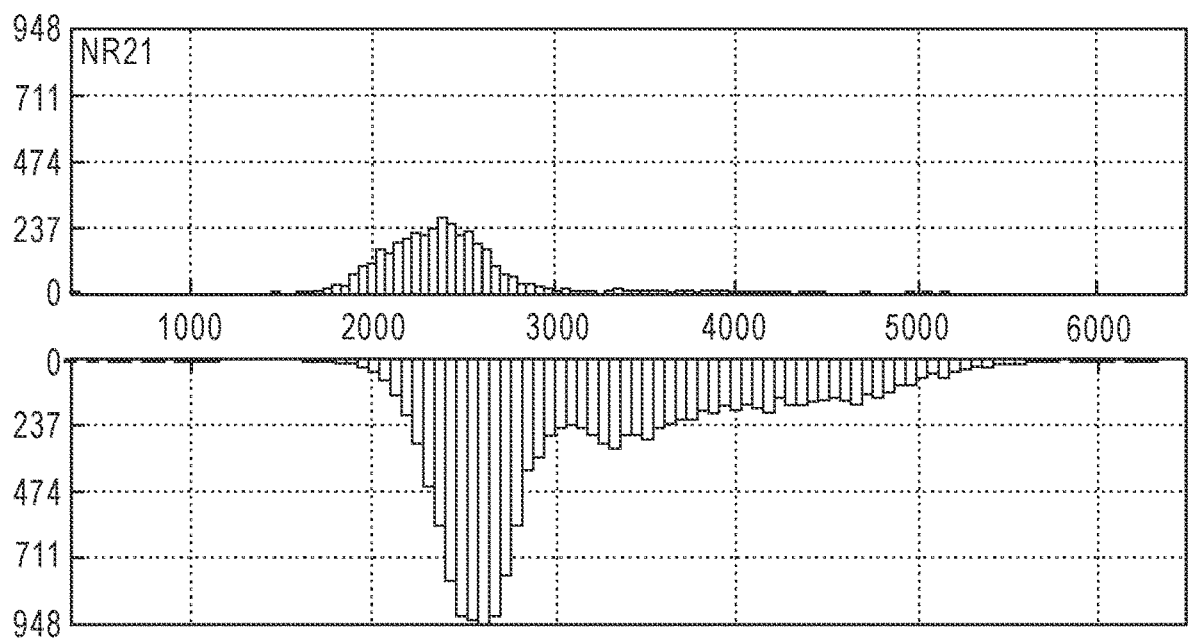
FIGS. 6A and 6B shows examples of histograms of HP signal values for tumor and normal samples.
Figure 6B:
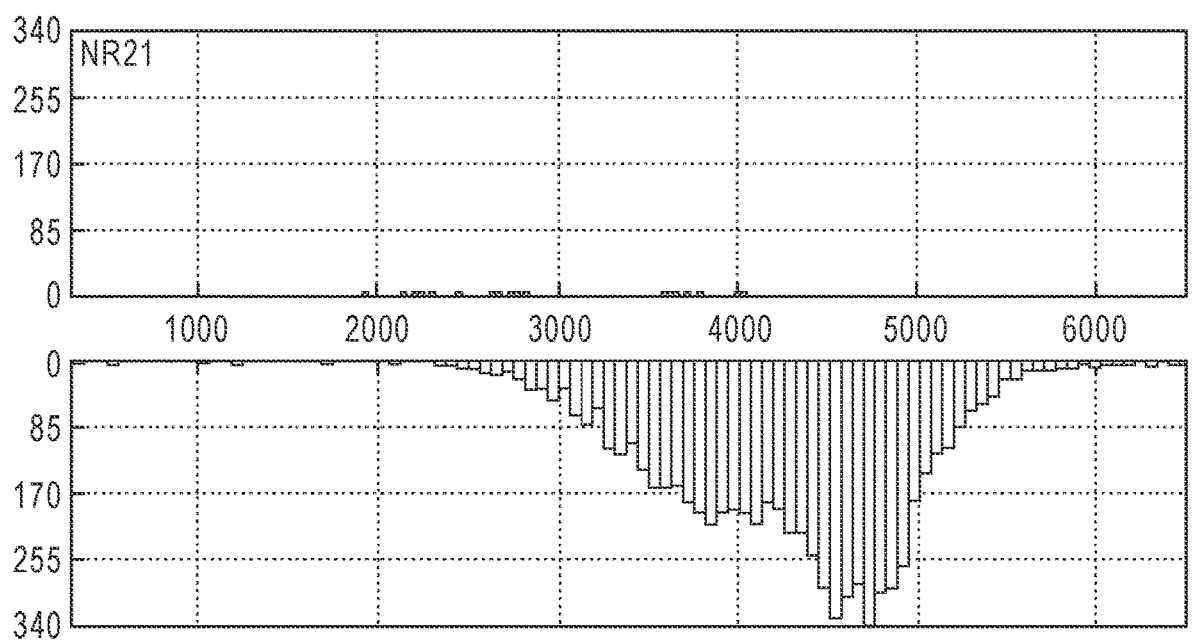

FIGS. 5A, 5B, 5C, 5D, 6A and 6B show examples of histograms of HP signal values for tumor and normal samples. The histograms are the results of the above step A.3 for sequence reads of long homopolymers corresponding to marker BAT25 (FIGS. 5A and 5B), the marker BAT26 (FIGS. 5C and 5D) and the marker NR21 (FIGS. 6A and 6B). The x-axis gives the HP signal values resulting from summing the flow space signal measurements, as in step A.3. The y-axis gives the number of sequence reads. Histograms of HP signal values for the sequence reads in the forward direction are above the x-axis and histograms of HP signal values for the sequence reads in the reverse direction are below the x-axis. The histograms of HP signal values for the tumor samples, given in FIGS. 5A, 5C and 6A, show several differences from those of the normal samples, given in FIGS. 5B, 5D and 6B. The differences for the HP signal values for the tumor samples compared to the normal samples include shifts to the left indicating lower HP signal values due to shortened homopolymers, wider ranges and multi-modal distributions.

In some embodiments, the features of the HP signal histogram may be based on the mean and standard deviation of the HP signal values. The score per marker using these features may be calculated as follows:

A.i) Calculate the mean and standard deviation (std) of the HP signal values for a control to form $mean_{CTL}$ and $std_{CTL}$.

A.ii) Calculate the mean and standard deviation of the HP signal values for a sample to form $mean_{SAMP}$ and $std_{SAMP}$.

A.iii) Calculate a mean difference=$(mean_{CTL}-mean_{SAMP})/std_{CTL}$.

A.iv) Calculate a std difference=$std_{SAMP}-std_{CTL}$.

In some embodiments, a first feature, $f_1$ is the mean difference calculated in step A.iii) above and a second feature $f_2$ is the std difference calculated in A.iv) above. In some embodiments, the score per marker may be calculated by a weighted sum:

$$\text{Score per marker} = a_1 f_1 + a_2 f_2 \qquad (1)$$

where $a_1$ and $a_2$ are weights.

In some embodiments, a sigmoid function S may be applied to the features to give $S(f_1)$ and $S(f_2)$. The sigmoid function may be useful for filtering out noise. In some embodiments, the score per marker may be calculated by a weighted sum of the sigmoid functions of the features:

$$\text{Score per marker} = a_1 S(f_1) + a_2 S(f_2) \qquad (2)$$

Figure 7:
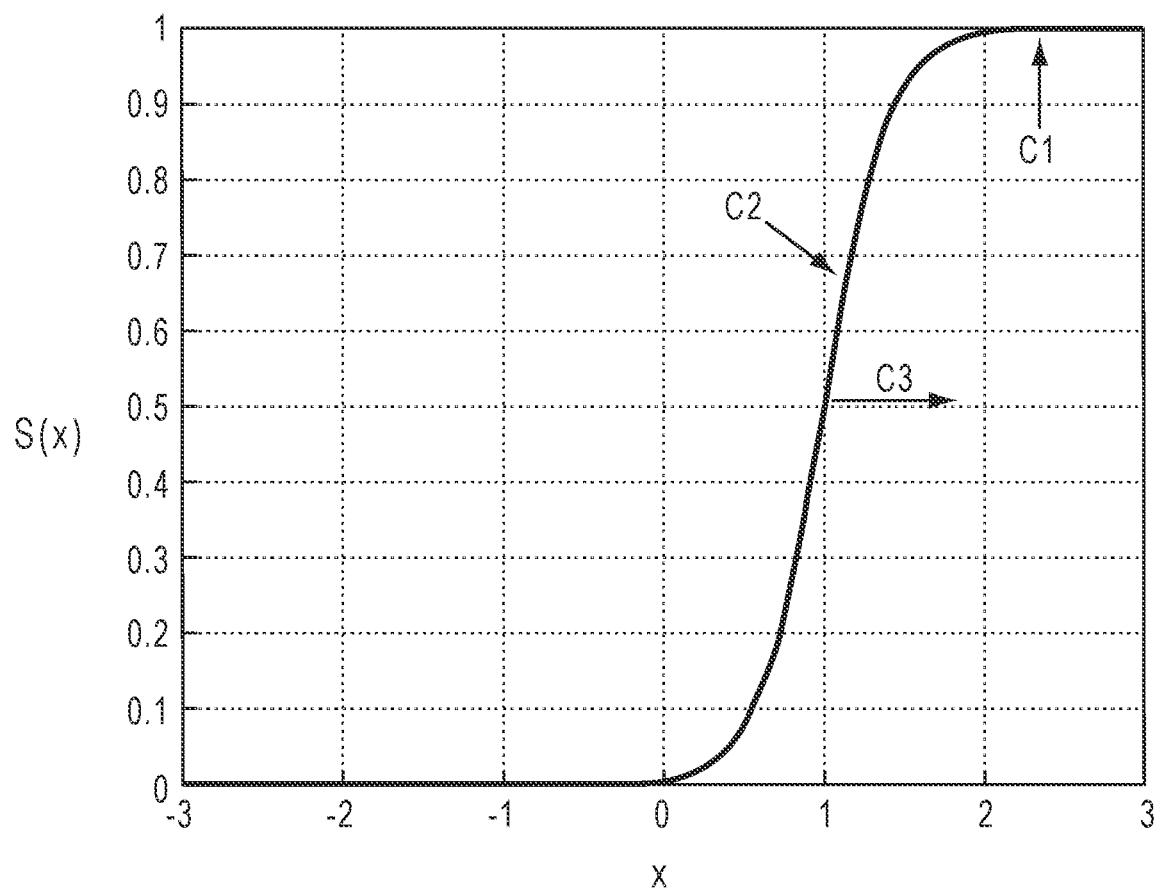
FIG. 7 is a plot of an example of a sigmoid function.

In some embodiments, the sigmoid function $S(x)$ is given by $$S(x) = C1/(1+\exp(-C2*(x-C3))) \qquad (3)$$

where C1 determines the maximum height of the sigmoid, C3 determines the shift and C2 determine the slope of the sigmoid. FIG. 7 shows an example of a sigmoid function.

In some embodiments, the control measurements may be obtained by sequencing an on-chip control sample. For example, the on-chip control sample may be provided by control genomic DNA from CEPH Individual 1347-02 (ThermoFisher Scientific catalog no. 403062) or Raji genomic DNA (part of TaqMan™ RNase P Detection Reagents Kit, ThermoFisher Scientific catalog no. 4316831). In some embodiments, the on-chip control sample may be sequenced in the same sequencing run as the test sample. The sequence reads for the on-chip control sample corresponding to the marker regions of interest are analyzed as described above to determine the HP signal values, $mean_{CTL}$ and $std_{CTL}$.

Advantages of using an on-chip control sample include providing accurate determinations of the $mean_{CTL}$ and $std_{CTL}$ for a given run that capture chip to chip variabilities and run to run variabilities in flow space signal values due to variations in chip gain and chemical buffering behavior. The flow space signal measurements for the on-chip control sample may be obtained during the same sequencing run as for the sample being tested, or test sample. The sequence reads for the on-chip control sample having the target homopolymer are identified as in step A.1 above. The HP signal values corresponding to the sequence reads for the on-chip control sample are calculated as in step A.2 above. The $mean_{CTL}$ and $std_{CTL}$ for the HP signal values for the on-chip control sample are calculated as in step A.i). The score per marker is determined using the mean difference for the sample and the on-chip control as determined in step A.iii) and the std difference determined by step A.iv) above. Since the $mean_{CTL}$ and $std_{CTL}$ are calculated for the same run as the $mean_{SAMP}$ and $std_{SAMP}$, chip to chip variabilities and run to run variabilities may not affect their values.

Figure 16A:
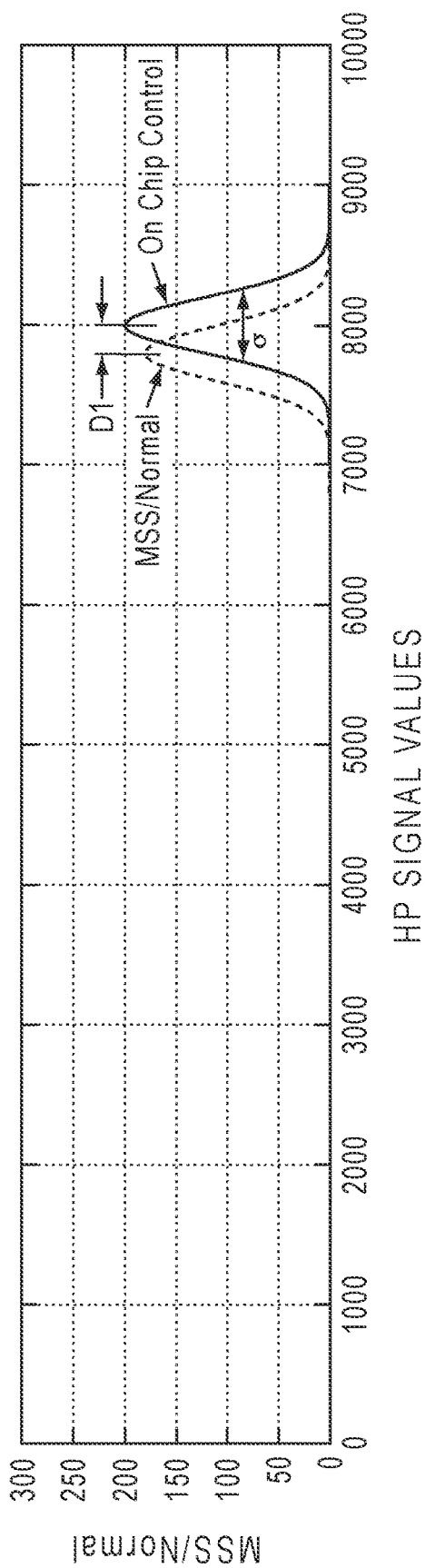
FIGS. 16A and 16B illustrate examples of distributions of homopolymer signal values for on-chip control, MSS/Normal and MSI-High.
Figure 16B:
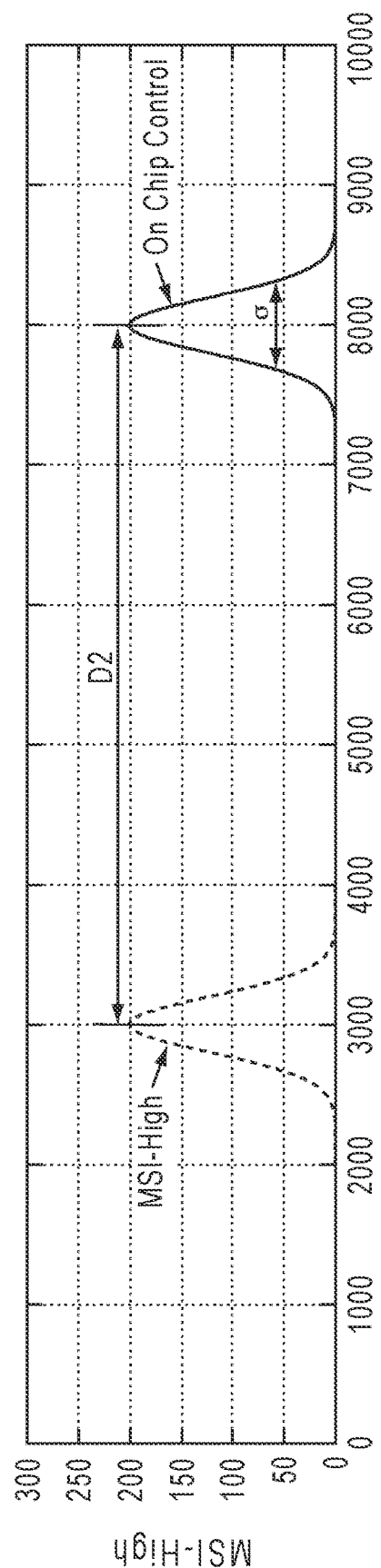

FIGS. 16A and 16B illustrate examples of distributions of homopolymer signal values for on-chip control, MSS/Normal and MSI-High. The distributions represent idealized histograms. FIGS. 16A and 16B show an example on-chip control distribution having $mean_{CTL}$=8000 and $std_{CTL}$=σ. FIG. 16A shows an example an MSS/Normal distribution having a $mean_{SAMP1}$ a distance of D1 from $mean_{CTL}$, where D1=($mean_{CTL}$−$mean_{SAMP1}$). FIG. 16B shows an example MSI-High distribution having a $mean_{SAMP2}$ a distance of D2 from $mean_{CTL}$, where D2=($mean_{CTL}$−$mean_{SAMP2}$).

However, the on-chip control sample occupies valuable space on the chip, in addition to the space occupied by the sample. In the case of higher multiplexing or a large panel, an increased number of markers in the control sample may reduce the coverages for some of the markers to below a minimum coverage, so that the scores for those markers may not be estimated.

In some embodiments, sequencing the on-chip control in one sequencing run can provide the $mean_{CTL}$ and $std_{CTL}$ that is stored for use as an in silico control for sequencing runs having no on-chip control sample. In this case, the step A.i) above is omitted and the stored values for the $mean_{CTL}$ and $std_{CTL}$ are used in steps iii) and iv). The in silico control positions may be measured using on-chip controls from previous runs having similar conditions, such as type of chip, chemistry and flow order. For detecting MSI status using a tumor-only analysis, stored values for $mean_{CTL}$ and $std_{CTL}$ can be used instead of sequencing an on-chip control from a normal sample to determine the per marker scores. The total MSI score can be determined by combining the per marker scores using the tumor-only analysis.

Figure 17A:
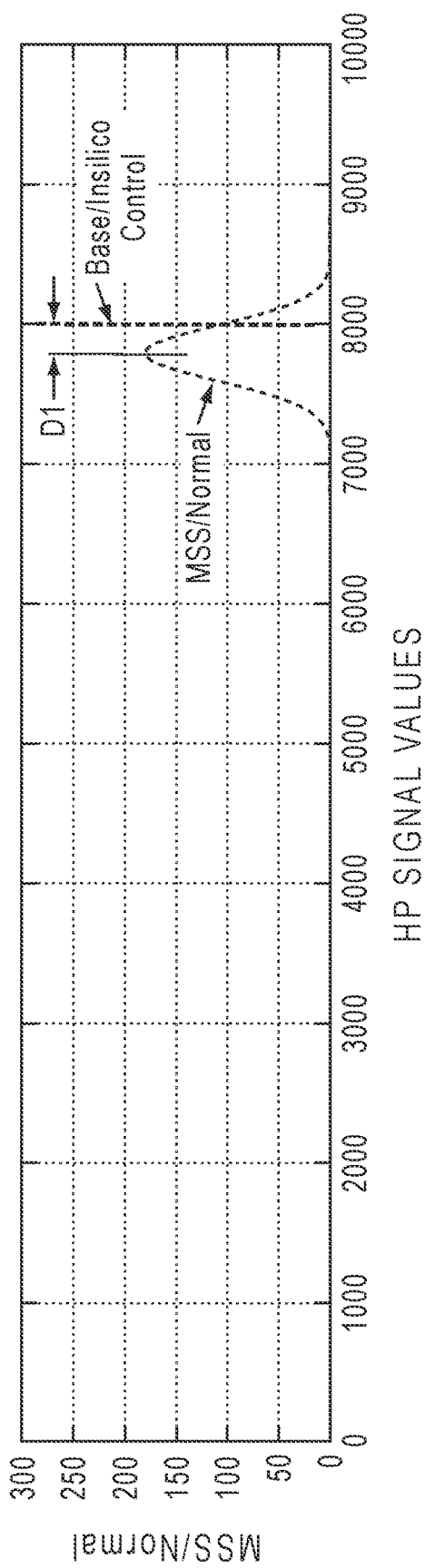
FIGS. 17A and 17B illustrate examples of distributions of homopolymer signal values for MSS/Normal and MSI-High and in silico control.
Figure 17B:
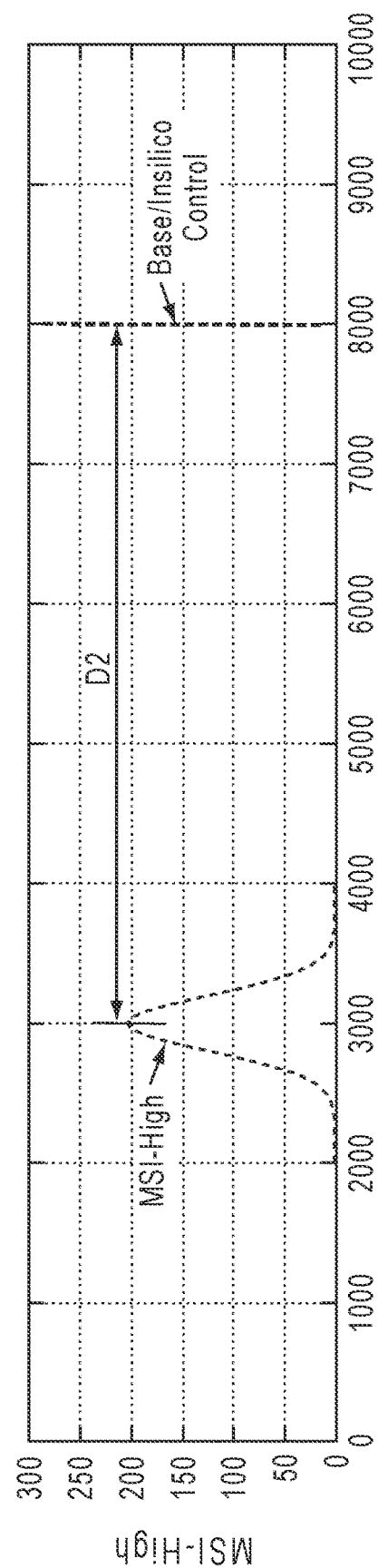

FIGS. 17A and 17B illustrate examples of distributions of homopolymer signal values for MSS/Normal and MSI-High and in silico control. FIGS. 17A and 17B show an example where the in silico control mean value, in silico $mean_{CTL}$=8000. For example, the value for in silico $mean_{CTL}$ may have been determined from a previous run using on-chip control as described with respect to FIGS. 16A and 16B. FIG. 17A shows an example MSS/Normal distribution having a $mean_{SAMP1}$ a distance of D1 from in silico $mean_{CTL}$, where D1=(in silico $mean_{CTL}$−$mean_{SAMP1}$). FIG. 17B shows an example MSI-High distribution having a $mean_{SAMP2}$ a distance of D2 from in silico $mean_{CTL}$, where D2=(in silico $mean_{CTL}$−$mean_{SAMP2}$).

An advantage of using the in silico control is that space on the chip for an on-chip control sample is not required. Another advantage is that in silico control is not affected by multiplexing or insufficient coverage of marker regions. This is because the in silico control values, e.g. $mean_{CTL}$ and $std_{CTL}$, corresponding to each of the marker regions are stored from a previous run. However, the in silico control does not capture run variabilities. The run variabilities may impact the calculated differences ($mean_{CTL}$−$mean_{SAMP}$) and ($std_{CTL}$−$std_{SAMP}$), possibly reducing the accuracy of the per marker score.

Figure 18A:
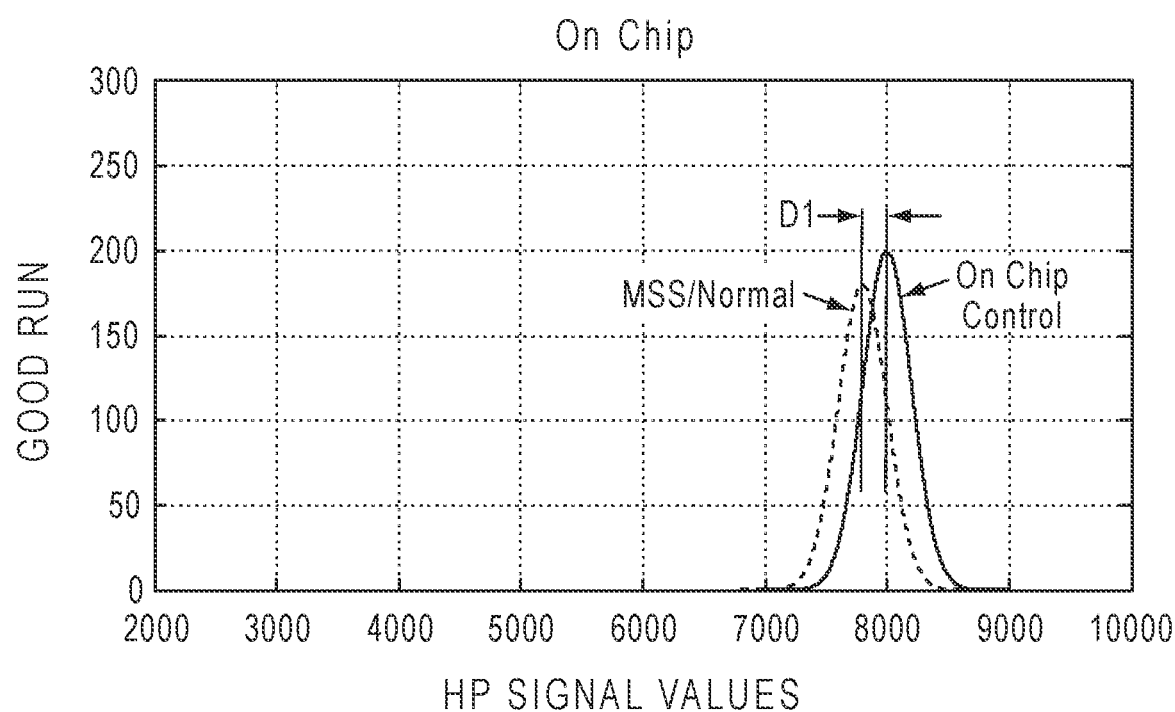
FIGS. 18A and 18B illustrate examples of distributions of homopolymer signal values for MSS/Normal for on-chip control and in silico control where there is low variability in chips and runs.
Figure 18B:
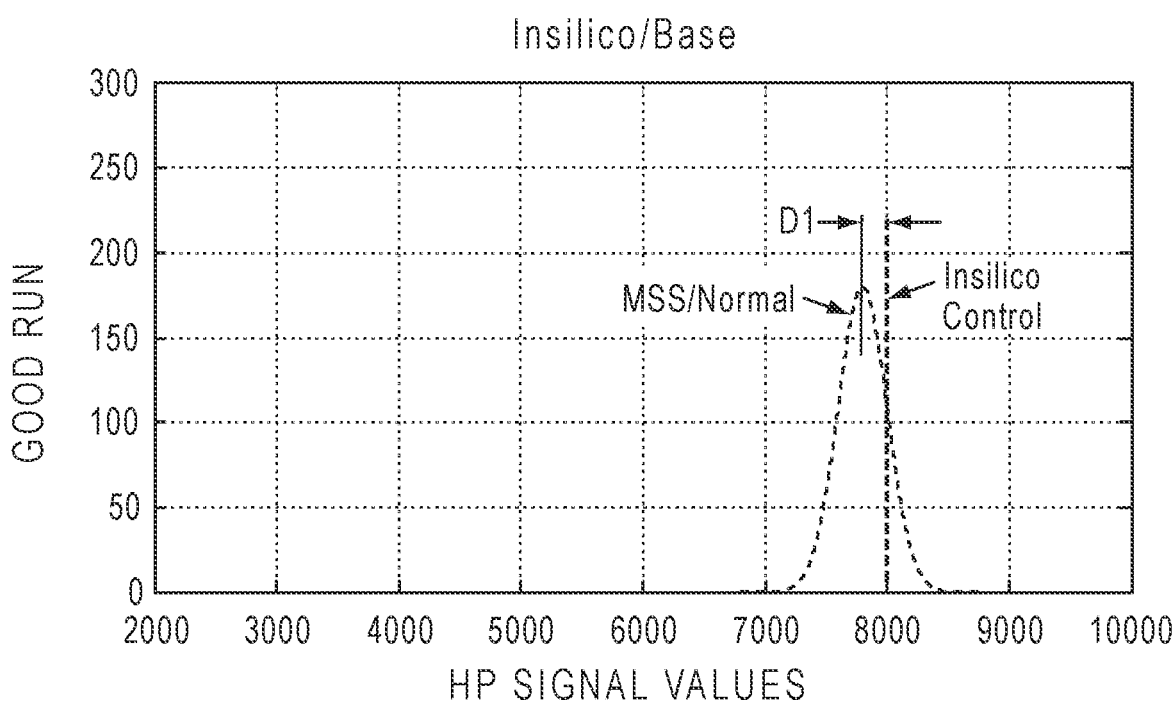

FIGS. 18A and 18B illustrate examples of distributions of homopolymer signal values for MSS/Normal for on-chip control and in silico control where there is low variability in chips and runs. FIG. 18A shows an example MSS/Normal distribution having a $mean_{SAMP}$ a distance of D1 from $mean_{CTL}$, where D1=($mean_{CTL}$−$mean_{SAMP}$), where $mean_{CTL}$ corresponds to an on-chip control sample. FIG. 18B shows an example MSS/Normal distribution having a $mean_{SAMP}$ a distance of D1 from $mean_{CTL}$, where D1=($mean_{CTL}$−$mean_{SAMP}$), where $mean_{CTL}$ corresponds to an in silico control calculated in a previous run. For low variability from run to run or from chip to chip, the in silico control can provide results for D1=($mean_{CTL}$−$mean_{SAMP}$) that are consistent with those with on-chip control.

Figure 19A:
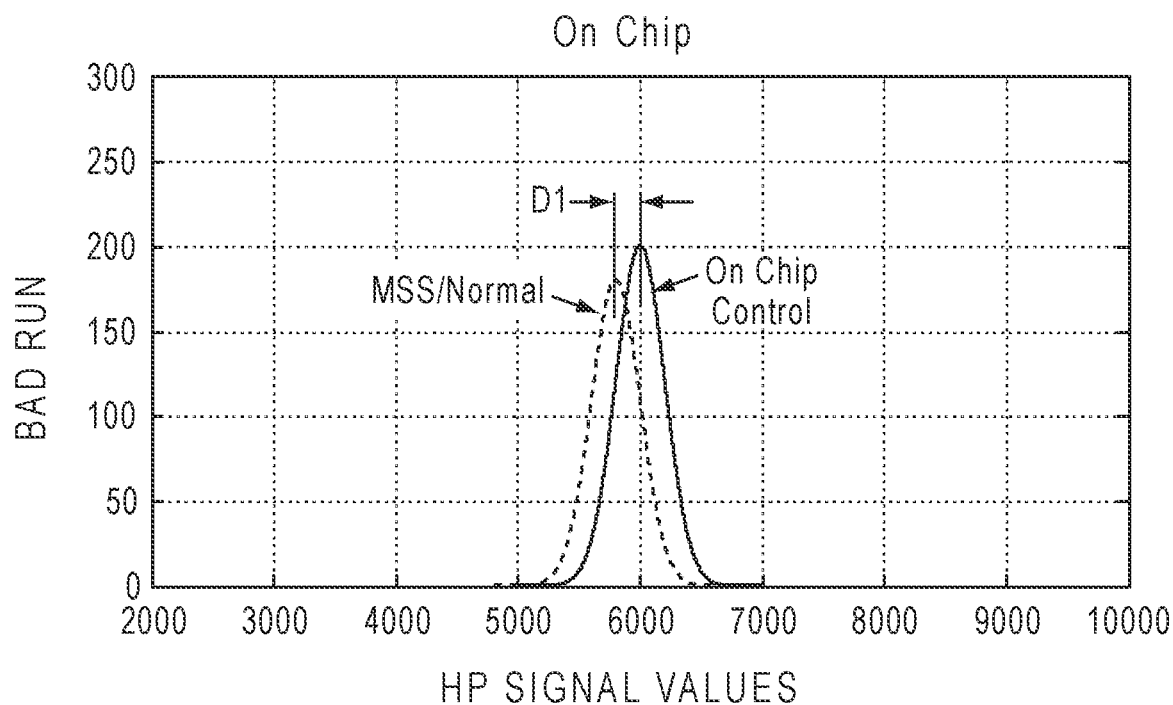
FIGS. 19A and 19B illustrate examples of distributions of homopolymer signal values for MSS/Normal for on-chip control and in silico control where there is high variability in chips and runs.
Figure 19B:
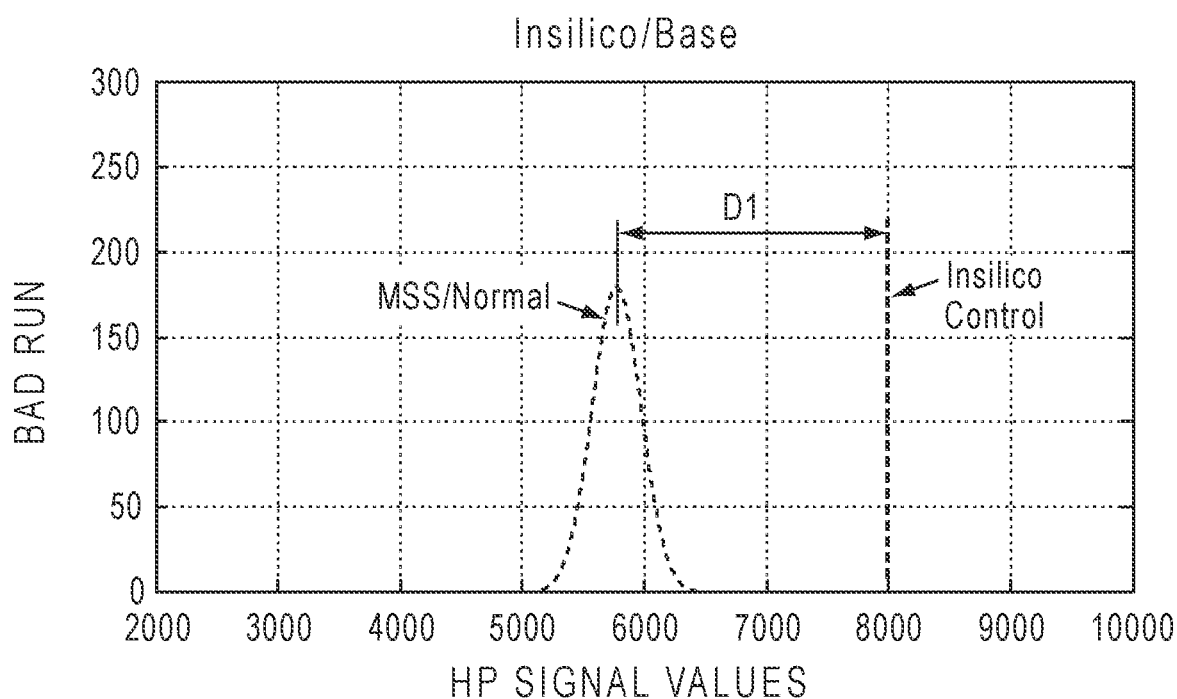

FIGS. 19A and 19B illustrate examples of distributions of homopolymer signal values for MSS/Normal for on-chip control and in silico control where there is high variability in chips and runs. FIG. 19A shows an example MSS/Normal distribution having a $mean_{SAMP}$ a distance of D1 from $mean_{CTL}$, where D1=($mean_{CTL}$−$mean_{SAMP}$), where $mean_{CTL}$ corresponds to an on-chip control sample. In FIG. 19A, both curves are shifted to lower HP signal values compared with those of FIG. 18A, however the distance D1 is the same for both FIGS. 18A and 19A. The on chip control is able to compensate for high variability from chip to chip and run to run. FIG. 19B shows an example MSS/Normal distribution having a $mean_{SAMP}$ a distance of D1 from $mean_{CTL}$, where D1=($mean_{CTL}$−$mean_{SAMP}$), where $mean_{CTL}$ corresponds to the same in silico control FIG. 18B. A shift in the MSS/Normal distribution due to variability of the chip or run, results in the D1 value of FIG. 19B that is significantly different than that of the example of FIG. 18B. The increase in D1 can produce an erroneous result in the mean difference calculation in step A.iii) above and an erroneous score per marker.

In some embodiments, the in silico control values for a given homopolymer calculated in a previous sequencing run may be modified in a using flow space signal measurements obtained in a current sequencing run. A combination of on-chip and in silico control is referred to herein as hybrid control. In hybrid control, the marker regions of an on-chip sample with sufficient coverage, for example at least 50 sequence reads, are used to estimate parameters of a transformation that can be applied to the in silico features to produce modified control features for a current run. In some embodiments, the test sample may include regions having monomorphic homopolymers. Monomorphic homopolymers have lengths that are stable in the human genome. These monomorphic homopolymer regions may be included in the gene panel for the test sample. When the on-chip sample is the test sample having monomorphic homopolymer regions, there may be no additional on-chip control sample required for the sequencing run. In other embodiments, there may be an on-chip control sample. In this case, certain markers for homopolymer regions in the on-chip control sample are selected if they have sufficient coverage, e.g. at least 50 sequence reads. The flow space signal measurements from the selected homopolymer marker regions are used to determine parameters of the transformation.

Figure 14:
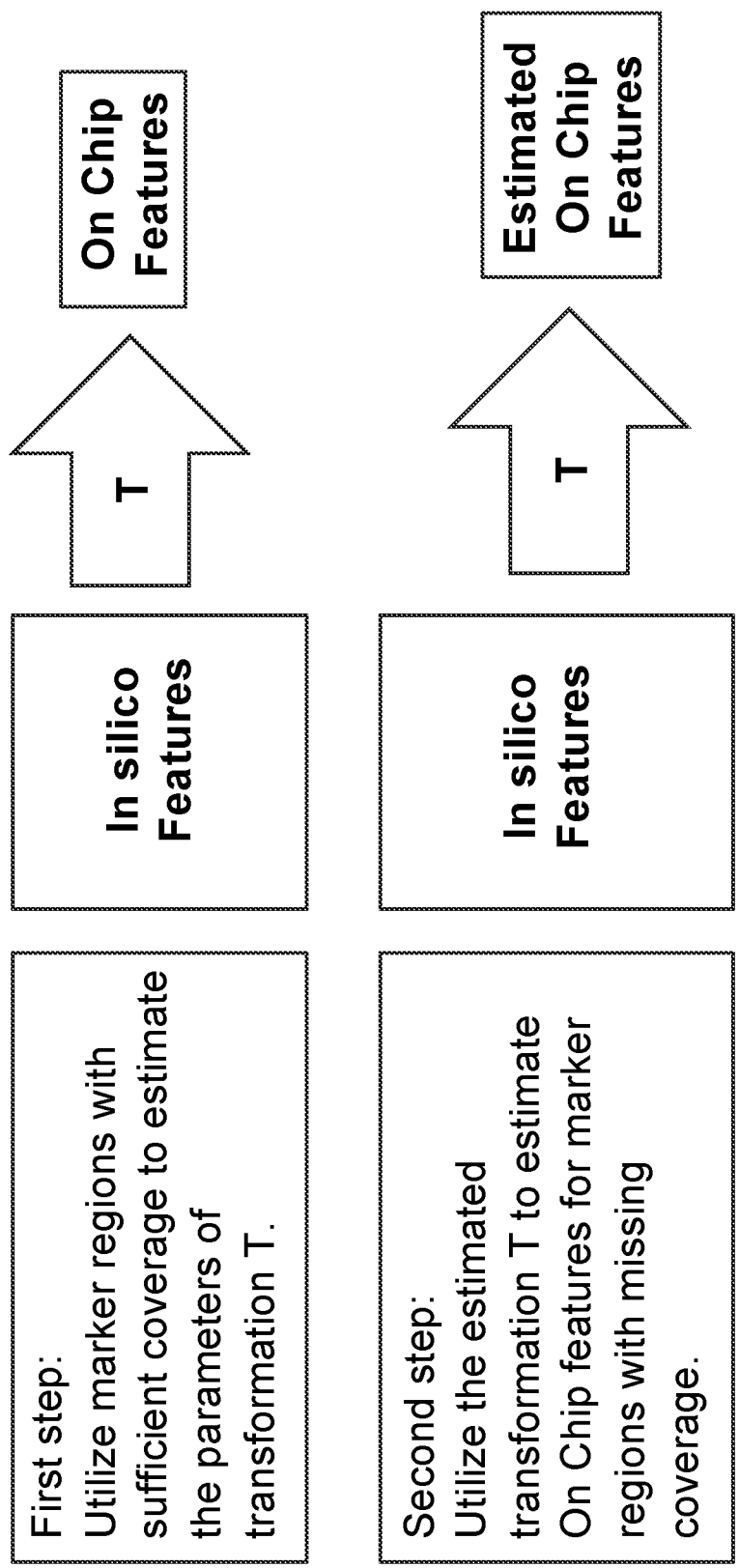
FIG. 14 is a block diagram of a method for hybrid control, according to an exemplary embodiment.

FIG. 14 is a block diagram of a method for hybrid control, according to an exemplary embodiment. The in silico features include the control values for one or more homopolymer marker regions calculated in a previous sequencing run. These in silico features may include the $mean_{CTL}$ values and $std_{CTL}$ values calculated for one or more homopolymer marker regions in an on-chip control sample in a previous run. In a first step, the parameters of a transformation T are calculated using flow space signal measurements corresponding to a selected set of homopolymer marker regions from the current run. The set of homopolymer marker regions from the current run may be selected based on sufficient coverage of the homopolymer region by the sequencing reads, for example 50 or more sequencing reads. The HP signal values corresponding to the sequence reads for the selected set homopolymer marker regions are calculated as in step A.2 above. The mean and standard deviation, $mean_{SEL}$, and $std_{SEL}$, for the HP signal values for each homopolymer in the selected set of homopolymer marker regions are calculated as in step A.i). The values for $mean_{SEL}$ for the selected set of homopolymers and the corresponding values for the same homopolymers in silico $mean_{CTL}$ values determined from the previous sequencing run may be used to determine the parameters of the transformation T. For example, the transformation T may comprise a polynomial function of the in silico $mean_{CTL}$ values. The parameters may be determined that minimize the error between the measured $mean_{SEL}$ and the estimated $mean_{SEL}$ values, where Estimated $mean_{SEL}$=T[in silico $mean_{CTL}$] (4)

Error=Estimated $mean_{SEL}$−Measured $mean_{SEL}$ (5)

For example, the parameters of T may be determined based on a minimum mean squared error criterion to achieve a linear or polynomial fit. In some embodiments, the set of homopolymer marker regions may be selected from the test sample having monomorphic homopolymer regions with sufficient coverage. Monomorphic homopolymers having homopolymer lengths between 8 and 14 are more likely to have sufficient coverage. For example, selecting monomorphic homopolymers in the test sample having lengths of 8, 10, 12 and 14 may be used to calculate the measured $mean_{SEL}$ for each of the selected homopolymer lengths.

In some embodiments, the set of homopolymer marker regions may be selected from an on-chip control sample, where the selected homopolymer regions have sufficient coverage. The HP signal values corresponding to the sequence reads for selected homopolymer regions of the on-chip control sample may be calculated as in step A.2 above. The $mean_{SEL}$ and $std_{SEL}$ of the HP signal values for the selected homopolymer regions of the on-chip control sample may be calculated as in step A.i). The measured $mean_{SEL}$ may be used to determine the parameters of T, as described above with respect to FIG. 14.

Returning to FIG. 14, once the parameters of the transformation T have been determined, the transformation T can be applied to in silico features to produce estimated on-chip features for homopolymer marker regions with low coverage. The homopolymer regions with low coverage, e.g. fewer than 50 sequencing reads, have insufficient coverage for determination of control values $mean_{CTL}$ values and $std_{CTL}$ based on sequencing reads from a current run. For example, a hybrid control value for the mean, $[mean_{CNTL}]_{HYB}$, for a homopolymer marker region having a low coverage can be calculated using the in silico $mean_{CNTL}$ as follows:

$[mean_{CNTL}]_{HYB}$=T$[mean_{CNTL}]_{IN\ SILICO}$ (6)

The hybrid control value $[mean_{CNTL}]_{HYB}$ may be used for $mean_{CNTL}$ in step A.iii) above to calculate the mean difference. It has been observed that the standard deviations for the selected homopolymer marker regions do not vary significantly from those of the in silico control. Determining parameters for a transformation and applying a transformation to the standard deviation values for the in silico control may be optional or not needed.

In some embodiments, synthetic calibration control strands may be provided along with the test sample for the sequencing run. The synthetic calibration control (SCC) strands may include synthetic DNA strands having homopolymers of known lengths. The synthetic DNA strand may be structured to have a homopolymer of the desired length, a left flank region on the 5' side of the homopolymer, a right flank region on the 3' side of the homopolymer, a 5' primer adjacent to the left flank region and a 3' primer adjacent to the right flank region. The primers may be targeted to amplify MSI marker regions of interest in the MSI panel content. In some embodiments, the SCC may not correspond to the MSI markers targeted in the panel and may be unique sequences that are identified by a unique reference sequence. The synthetic homopolymers may be structured to have base types and lengths relevant for the marker regions of interest. For example, if the MSI panel includes marker regions of interest that include homopolymers of A and homopolymers of T, the synthetic calibration control strands may include homopolymers of A and homopolymers of T. For example, the lengths of the synthetic homopolymers in the SCC strands may be 13 to 30 bases. In some embodiments, there may be 3-4 different lengths of homopolymers for a marker region of interest. For example, for 9 different MSI markers of interest in a MSI panel, the SCC amplicons for each marker may include 3-4 different HP lengths. Examples of other numbers of HP lengths for each marker include 1, 1-2 or 2-3.

In some embodiments, the synthetic calibration control may include a first tag sequence in the left flank region and a second tag sequence in the right the right flank region. The first tag sequence is substituted for the sequence of bases that occur in the reference sequence at specific locations in the left flank region. The second tag sequence is substituted for the sequence of bases that occur in the reference sequence at specific locations in the right flank region. The tag sequences may be 3-4 bases in length. The tag sequences allow the SCC sequence reads to be identified in the aligned sequence read information provided in an aligned BAM file, for example, after alignment with the reference sequence. The tag sequence lengths may be 3-4 so that the mapping of the sequence reads to the reference sequence may provide aligned SCC sequence reads, although there may be mismatches between the tag sequences and the corresponding locations in the reference sequence.

FIG. 20 gives examples of synthetic calibration control sequences and a reference sequence from hg19. In this example, the marker region of interest in the reference sequence has an HP length of 18 A's. The first exemplary SCC sequence has an HP length of 18 A's. The second exemplary SCC sequence has an HP length of 14 A's. The third exemplary SCC sequence has an HP length of 22 A's. These exemplary SCC sequences each have a tag sequence in the left flank region and a tag sequence in the right flank region. The tag sequences substitute 3 or 4 bases for bases in the corresponding 3 or 4 positions in the reference sequence. For example, for "CATT" in the left flank of the reference sequence, the first exemplary SCC sequence may substitute the tag "GATG" in its left flank. For example, for the "AAT" in the right flank of the reference sequence, the first exemplary SCC sequence may substitute the tag "TAC" in its right flank. For example, the second exemplary SCC sequence, the tag "GAT" may substitute for reference's "ATT" in the left flank and the tag "CGT" may substitute for the reference's "AAT" in the right flank. For example, the third exemplary SCC sequence, the tag "TGA" may substitute for reference's "ATT" in the left flank and the tag "GCG" may substitute for the reference's "AAT" in the right flank.

In some embodiments, Invitrogen GeneArt Gene Synthesis available from ThermoFisher Scientific, or DNA synthesis from other vendors, may be used to generate the synthetic DNA for the SCC sequences. The synthetic DNA for the SCC sequences may be amplified together with the test sample DNA in the presence of a primer pool targeting the MSI markers of interest. The SCC amplicons and the sample amplicons may be sequenced as described below to form sequence reads corresponding to the SCCs and the sample. The sequence reads may be mapped to the reference sequence to form aligned sequence read information for an aligned BAM file.

In some embodiments, the sequence reads for the target homopolymer corresponding to the marker are identified as described above for the homopolymer classifier in step A.1. The left flank region and right flank region of the aligned sequence reads are analyzed to detect the presence of tag sequences. If the tag sequences are detected, the particular tag sequences identify the corresponding SCC sequence. If the tag sequences are not detected, the sequence read may correspond to the sample being tested. For each SCC sequence read, calculate a sum of M flow space signal measurements corresponding to M nucleotide flows of the sequence of flows having the same HP nucleotide type as the target homopolymer to form a HP signal value for the SCC sequence read, as in step A.2 above. As in step A.3 above, calculate a histogram of HP signal values for the SCC sequence reads in the forward direction and a histogram of HP signal values for the SCC sequence reads in the reverse direction. As in step A.i) above, calculate the $mean_{SCC}$ and $std_{SCC}$ for the histogram of HP signal values for each of the SCC sequence reads.

Figure 21A:
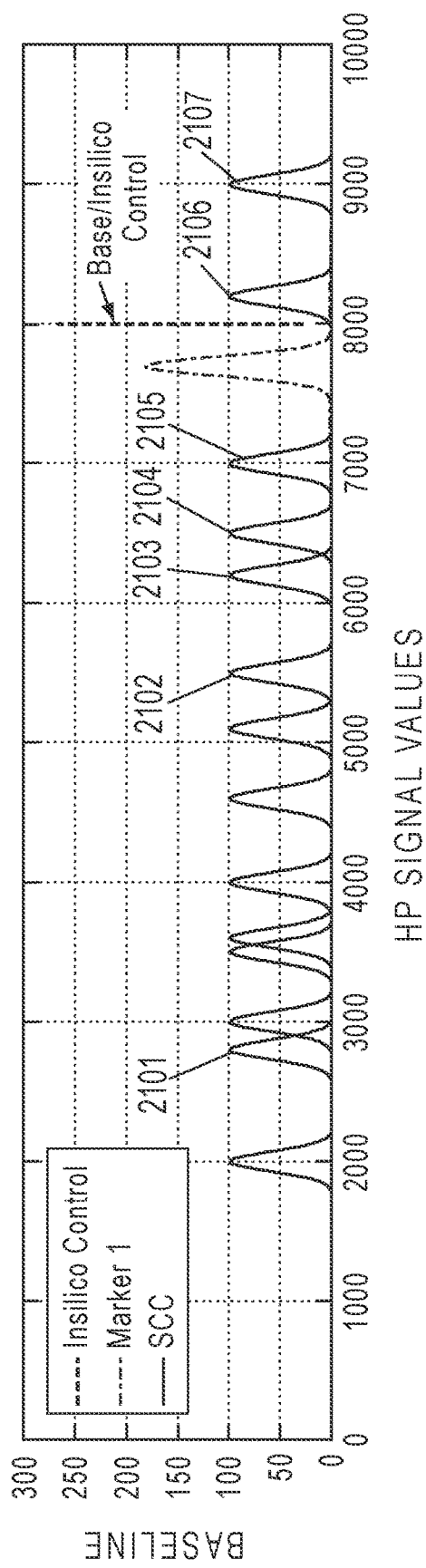
FIGS. 21A and 21B illustrate examples of distributions of HP signal values for SCC sequence reads for a group of SCC markers and a distribution HP signal values for sequence reads of a test sample at a given marker.
Figure 21B:
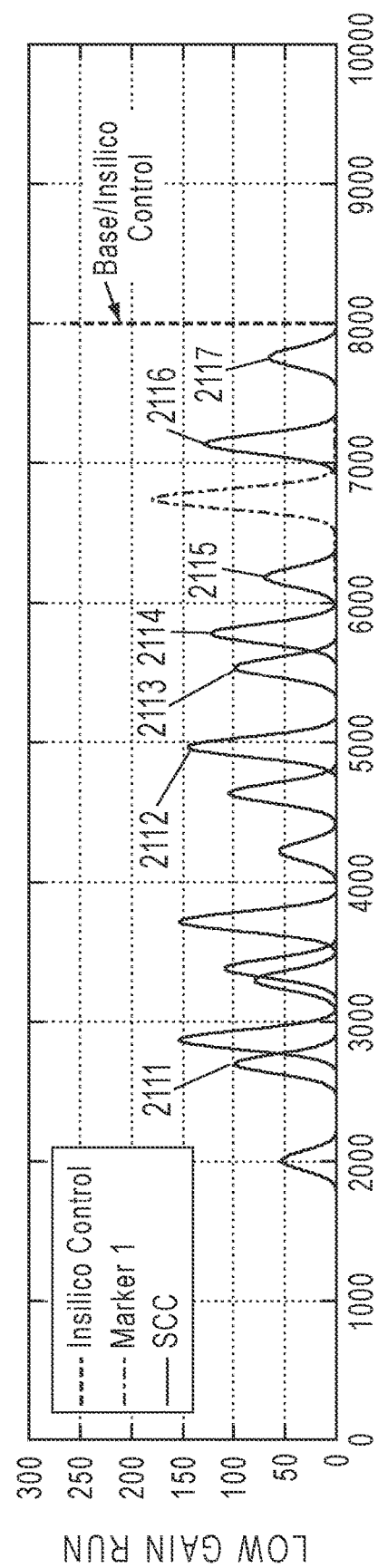

FIGS. 21A and 21B illustrate examples of distributions of HP signal values for SCC sequence reads for a group of SCC markers and a distribution HP signal values for sequence reads of a test sample at a given marker. The distributions of HP signal values for the SCC sequence reads correspond to various known HP lengths. The position on the x-axis of each peak value corresponds to the mean value. FIG. 21A shows examples of baseline distributions of HP signal values of SCC sequence reads, including distributions 2101, 2102, 2103, 2104, 2105, 2106 and 2107. The baseline in silico control reference value is also indicated. The j-th baseline mean value, $mean_{BASELINE}(j)$, of the distributions for the j-th SCC and the in silico control value can be stored in a configuration file. FIG. 21B shows how a low gain sequencing run can affect the distributions of HP signal values for the SCCs and the test sample. For the low gain sequencing run, the distributions of HP signal values are non-uniformly shifted, where higher values are shifted more than lower values. For example, the distributions 2111, 2112, 2113, 2114, 2115, 2116 and 2117 are shifted relative to the corresponding distributions 2101, 2102, 2103, 2104, 2105, 2106 and 2107 in FIG. 21A. The distribution of HP signal values for the marker 1 are shifted further from the in silico control value, which could lead to an erroneous MSI score for that marker.

Figure 22A:
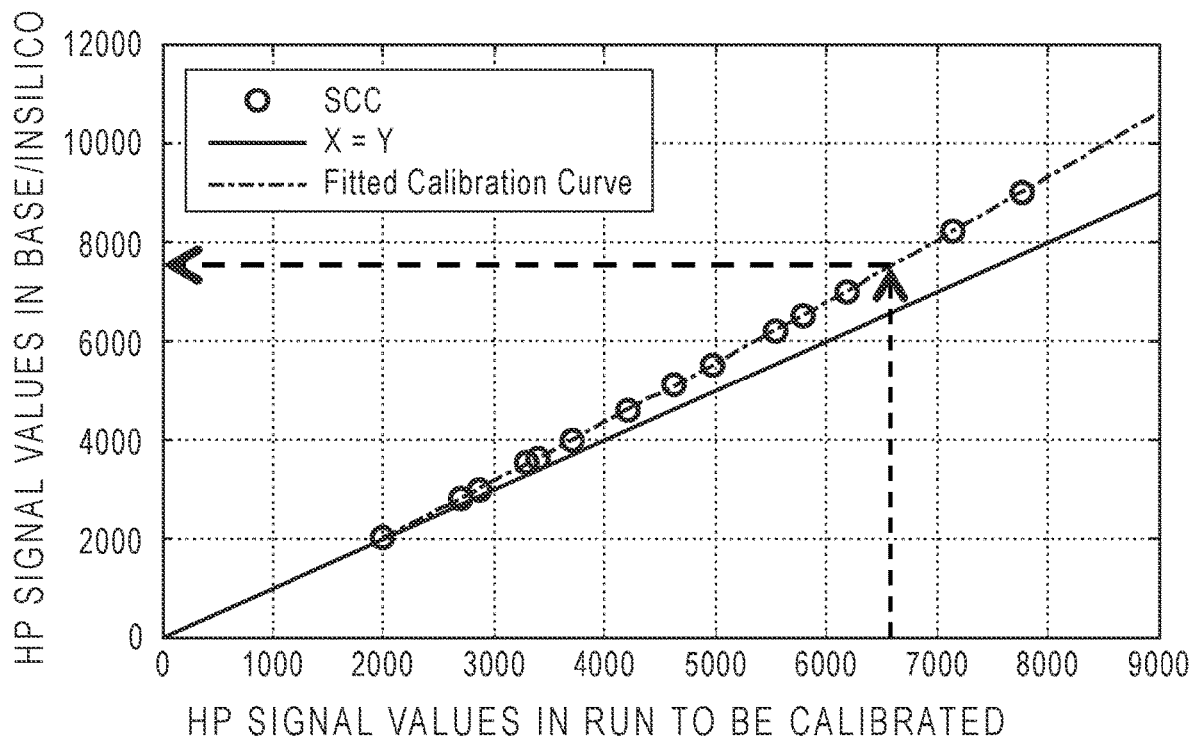
FIG. 22A illustrates an example of a polynomial fit to generate a fitted calibration curve for the examples shown in FIGS. 21A and 21B.

In some embodiments, a correction can be applied to HP signal values of the distributions corresponding to the SCCs and the distribution corresponding to the test sample at the marker to correct for the distortion in a current run. The baseline mean value, $mean_{BASELINE}(j)$, for each j-th SCC in a baseline run can be modeled as a polynomial function of the mean value, $mean_{CURRENT}(j)$ for a current run. FIG. 22A illustrates an example of a polynomial fit to generate a calibration curve for the examples shown in FIGS. 21A and 21B. The x-axis gives the HP signal values for the current run to be calibrated. The y-axis gives the HP signal values for the baseline. The circles indicate the $mean_{CURRENT}(j)$ on the x-axis mapped to the $mean_{BASELINE}(j)$ on the y-axis for the j-th SCC. A polynomial function $y=f(x)$ may be fitted using various approaches, such as a least squares method, to generate a calibration curve, where, $$mean_{BASELINE}(j)=f[mean_{CURRENT}(j)] \quad (7)$$

for the HP lengths of the SCCs. The fitted polynomial function can then be applied to the mean of the HP signal values for the test sample for each homopolymer marker, $mean_{MARKER}$. The polynomial function can have any suitable order, such as first order (linear function), second order (quadratic function) or a higher order. The polynomial function maps the $mean_{MARKER}$ value to a corrected $mean_{MARKER}$ value, where, $$corrected\ mean_{MARKER}=f[mean_{MARKER}] \quad (8)$$

Figure 22B:
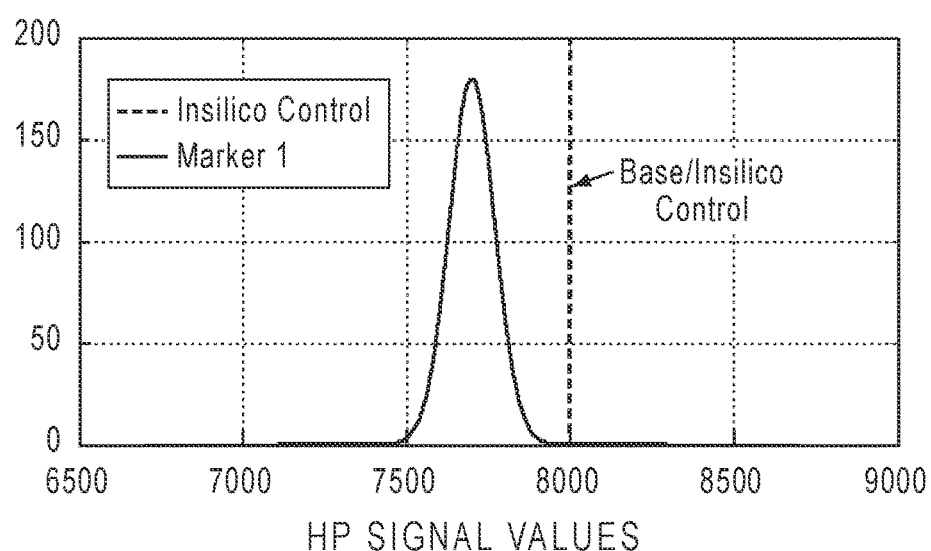
FIG. 22B shows an example of the correction of the distribution of the HP signal values for the test sample at the marker for the examples of FIGS. 21A and 21B.

The dashed arrows in FIG. 22A illustrate this mapping by the polynomial function. FIG. 22B shows an example of the correction of the distribution of the HP signal values for the test sample at the marker for the examples of FIGS. 21A and 21B. The corrected distribution of HP signal values for the test sample at the marker is restored to the position in the baseline plot of FIG. 21A. The distance between the corrected $mean_{MARKER}$ value and the in silico control value is the same as in the baseline plot of FIG. 21A. The calculation of the mean difference, as in step A.iii) above, using the corrected $mean_{MARKER}$ value and the in silico control value for $mean_{CTL}$ is given by, $$mean\ difference=(mean_{CTL}-corrected\ mean_{MARKER})/std_{CTL} \quad (9)$$

In some embodiments, a method for determining a score per marker corresponding to a marker region having a long homopolymer using synthetic calibration controls may comprise the steps of a) generating synthetic calibration control (SCC) nucleic acid strands having known homopolymer portions with known lengths and tag sequences, b) amplifying the SCC nucleic acid strands and a nucleic acid test sample in the presence of a primer pool targeting the MSI markers of interest to produce a plurality of amplicons, c) sequencing the amplicons to generate a plurality of sequence reads, d) mapping the sequence reads to a reference sequence, wherein the reference sequence includes the MSI marker regions of interest, for each marker region: e) identifying tag sequences in the SCC sequence reads, f) for each sequence read, calculate a sum of flow space signal measurements corresponding to nucleotide flows having the same nucleotide type as the target homopolymer to form a homopolymer (HP) signal value for the sequence read, g) generating a histogram of HP signal values for the sequence reads of the marker region, h) calculating a mean value for the histogram of HP signal values for the SCC sequence reads corresponding to each homopolymer length, i) determining a polynomial function that maps the mean value corresponding to each HP length to baseline mean values, j) calculating a mean value of the histogram of HP signal values for the test sample for each marker region to form a marker mean value, k) applying the polynomial function to each marker mean value to form a corrected marker mean value, l) calculating a difference between an in silico control mean value and the corrected marker mean value, m) calculating a standard deviation of the histogram of HP signal values for the test sample for the marker region to form a marker standard deviation, n) calculating a difference between the marker standard deviation and an in silico standard deviation, and o) determining a score for the marker based on mean difference and the standard deviation difference.

In some embodiments, the STR classifier determines an MSI score per marker for the aligned sequence reads corresponding to a marker region having dinucleotide repeats or STR by applying the following steps to sequence reads obtained by sequencing a tumor sample:

B.1) Identify sequence reads having the left flank sequence for the target dinucleotide repeat or STR corresponding to the marker.

B.2) For each sequence read in base space, count the number of repeats of the repeated sequence of bases. Counts for individual bases that do not form a complete repeat sequence are given to the right of the decimal point. For example, a count of 10.2 for a sequence read indicates 10 repeats of the complete repeat sequence and 2 additional bases of a partial repeat.

B.3) Calculate a histogram of repeat lengths of the number sequence reads versus the number of repeats.

B.4) Calculate a score per marker for the dinucleotide repeat or STR based on features of the histograms.

Figure 8A:
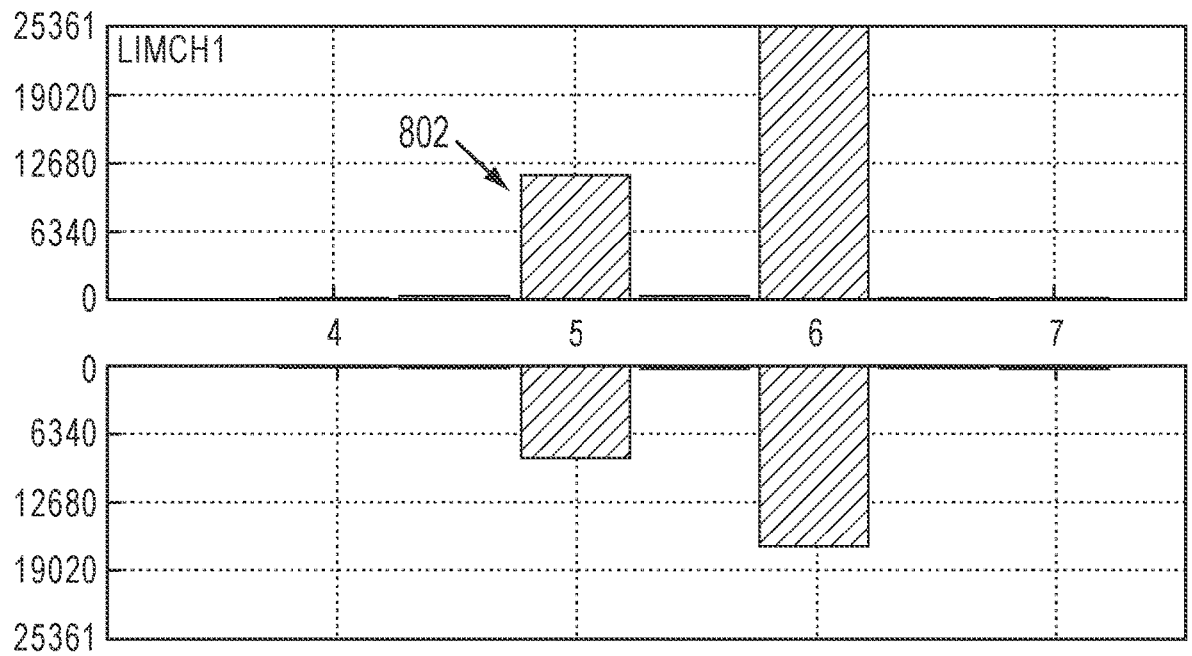
FIGS. 8A-8D show examples of histograms of repeat lengths for MSI-H and matched normal samples.
Figure 8B:
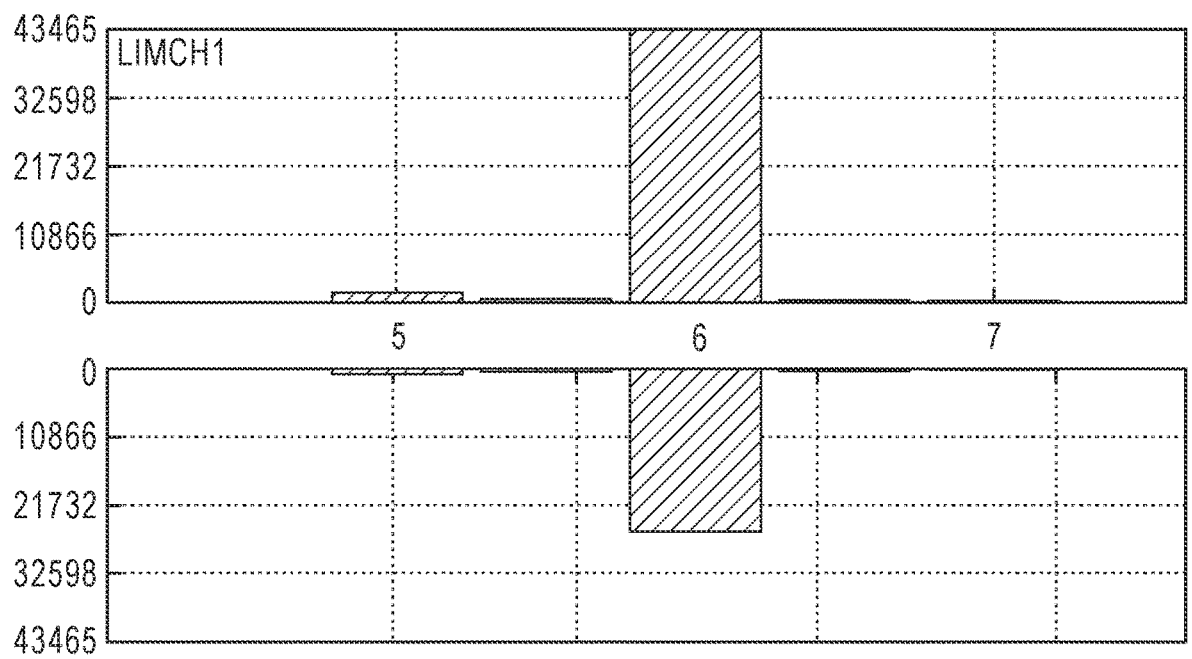
Figure 8C:
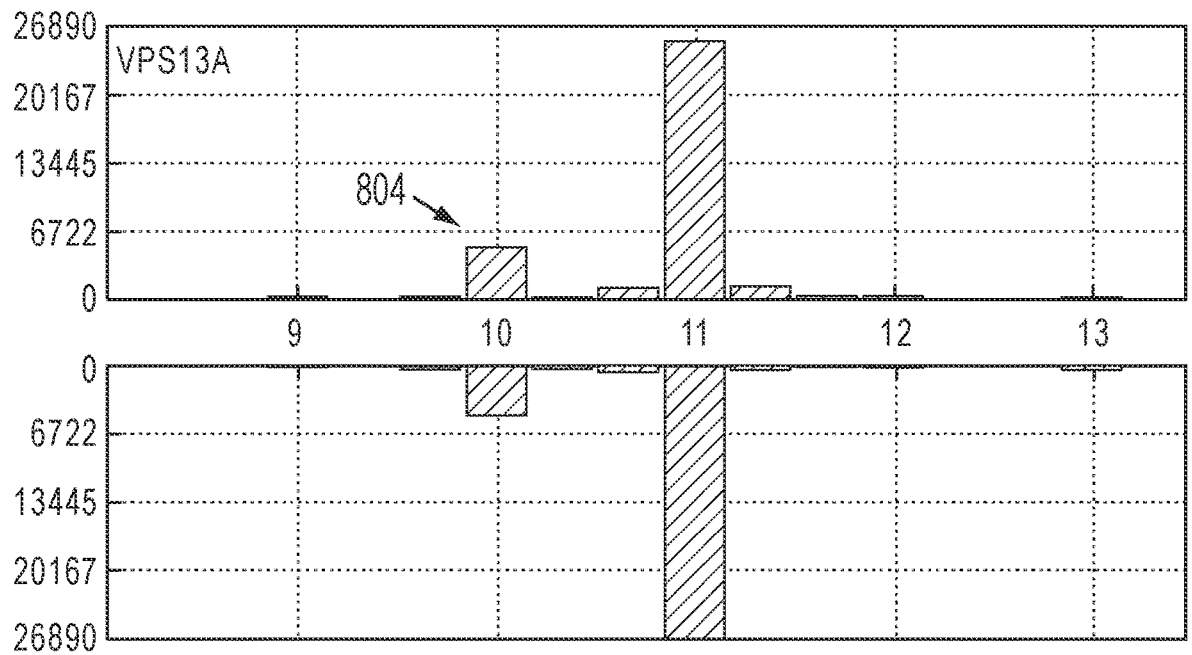
Figure 8D:
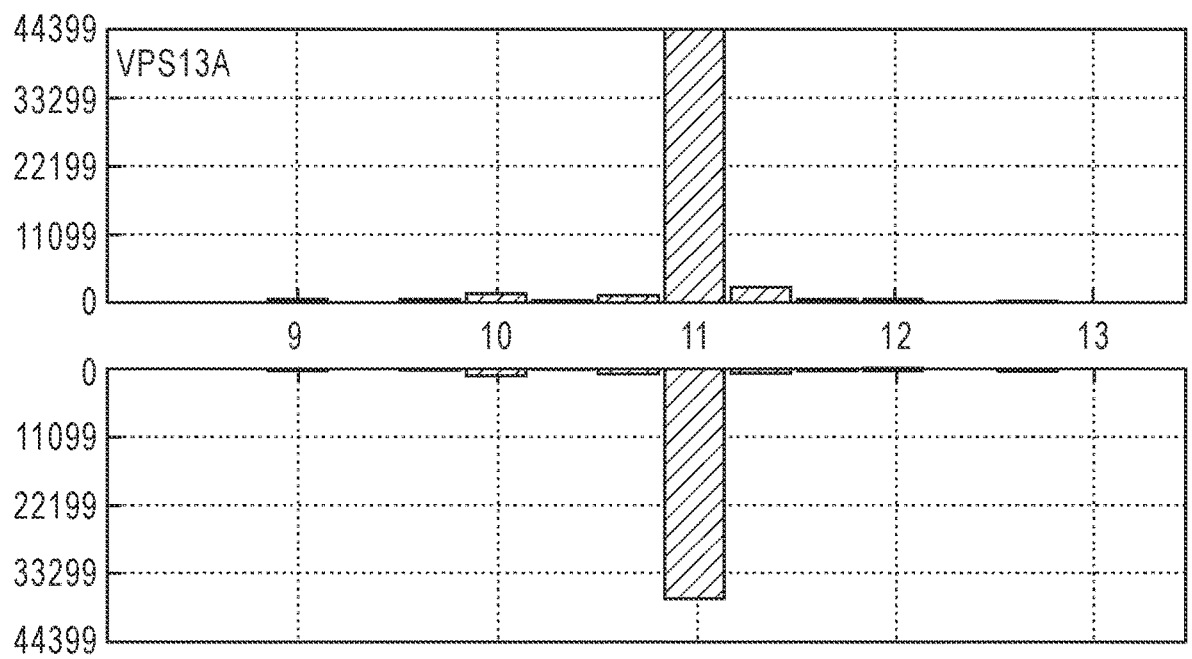

FIGS. 8A and 8B show examples of histograms of repeat lengths for MSI-H (8A) and matched normal samples (8B) of dinucleotide repeats corresponding to the marker LIMCH1. FIGS. 8C and 8D show examples of histograms of repeat lengths for MSI-H (8C) and matched normal samples (8D) of trinucleotide repeats corresponding to the marker VPS13A. The x-axis gives the repeat length values. The y-axis gives the number of sequence reads. Histograms of repeat lengths for the sequence reads in the forward direction are above the x-axis and histograms of repeat lengths for the sequence reads in the reverse direction are below the x-axis. The histograms of repeat lengths for the MSI-H samples each show a second repeat length with a significant number of sequence reads while the normal samples each have one repeat length with a significant number of sequence reads.

In some embodiments, a first feature may include the histogram bin having the highest number of sequence reads and a second feature may include the histogram bin having the second highest number of sequence reads. Using these features, a score per marker for the dinucleotide repeat or STR may be calculated as follows:

B.a. Calculate a ratio of the second highest number of sequence reads to the first highest number of sequence reads in the histogram of repeat lengths.

B.b. Apply a sigmoid function to the ratio.

B.c. Multiply the output of the sigmoid function by a constant to give the score per marker for the dinucleotide repeat or STR.

B.d. Repeat steps a, b and c for sequence reads on forward and reverse strands.

In some embodiments, the multiplication by the constant may provide a common range for the score per marker for a dinucleotide repeat or STR and the score per marker for a long homopolymer. The constant may be determined by comparing a first range of MSI scores per marker for long homopolymers to a second range of MSI scores per marker for dinucleotide repeats or STRs in a truth set of samples where MSI status is known. The constant may be based on a ratio of the first range to the second range.

The STR classifier method described above can determine an MSI score per marker for STR regions in a tumor-only analysis. The histogram of repeat lengths may be calculated and analyzed for sequence reads obtained from tumor samples.

In some embodiments, a total score may be calculated based on the per marker scores, as follows:

B.I. Determine whether the sequence reads associated with the marker have a coverage levels greater than or equal to a minimum coverage level. For example a minimum coverage level may be 20 sequence reads.

B.II. Apply a threshold score to the score per marker calculated for the forward sequence reads and the reverse sequence reads for each of the markers and select the scores greater than or equal to the threshold score. The threshold score may be set by the user.

B.III. Sum the selected scores for the forward sequence reads meeting the minimum coverage criterion to produce a summed score for the forward sequence reads.

B.IV. Sum the selected scores for the reverse sequence reads meeting the minimum coverage criterion to produce a summed score for the reverse sequence reads.

B.V. Add the summed score for the forward sequence reads to the summed score for the reverse sequence reads to produce a total MSI score for the sample.

B.VI. If coverage levels for some markers do not meet the minimum coverage level in step B.I, normalize the total MSI score based on the number of markers having coverage levels greater than or equal to the minimum coverage level to produce the total MSI score for the sample. The normalization may be calculated as follows:

$$TS\_n = TS*(T/(T-N)) \quad (10)$$

where TS_n is the normalized total MSI score, TS is the total MSI score calculated in step B.V. T is the total number of markers and N is the number of markers that have less than the minimum coverage level in step B.I.

The total MSI score can be assigned to each sample using per marker MSI scores across multiple markers. The total MSI score can be used to evaluate MSI status. The total MSI score for a tumor only sample can be obtained when in silico control with stored values for $mean_{CTL}$ and $std_{CTL}$ are used by the homopolymer classifier method instead of sequencing an on-chip control from a normal sample. Thus, the MSI status can be evaluated with tumor only samples.

FIG. 9 gives an exemplary table of results of per marker scores and total MSI scores for several markers in six samples with known MSI status. The per marker scores and total MSI scores were determined by the methods described herein. The substantial differences in total MSI scores between the MSI-H samples and MSI-L samples demonstrate the ability of the total MSI score to discriminate between MSI-H and MSI-L status.

FIG. 10 gives an exemplary table of results of testing of MSI status using capillary electrophoresis (CE). FIG. 11 gives an exemplary table of results of testing of MSI status using the total MSI score determined by the NGS methods described herein. These exemplary results of orthogonal testing show that NGS results using the methods described herein are concordant with sample designation of MSI status found by CE.

Figure 15:
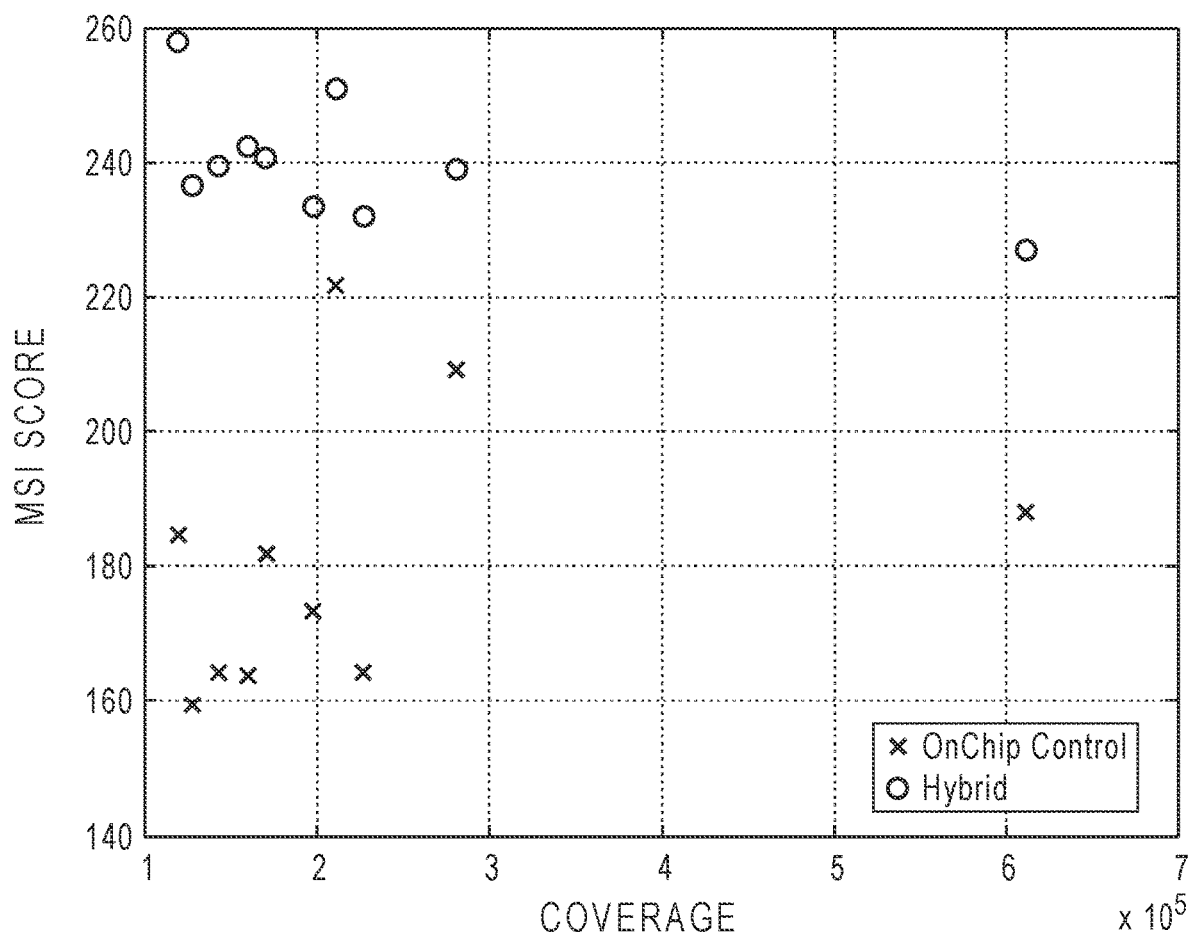
FIG. 15 gives a plot of exemplary results for MSI scores determined using on-chip control samples and hybrid control.

FIG. 15 gives a plot of exemplary results for MSI scores determined using on-chip control samples and hybrid control. The sequencing read data were generated from 10×, 20×, 30× and 40× multiplexing applied to the same biological sample in different runs. The MSI scores (y-axis) correspond to the total MSI scores, such as those given in the bottom line of FIG. 9. The read coverage (x-axis) is given in number of reads for the same sample resulting from multiple experiments. The coefficient of variation (CV) for the MSI scores is defined as the ratio of the standard deviation to the mean of the MSI scores. In this example, the MSI scores resulting from using the targeted homopolymer regions of on-chip control sample show variability ranging from MSI scores of 160 to 220. The coefficient of variation for the on-chip control, $CV_{ON\text{-}CHIP}$ is 11.4%. For the hybrid control, a set of the targeted homopolymer marker regions of the on-chip control sample were selected based on coverage. The selected homopolymer marker regions were used to determine hybrid control values $[mean_{CNTL}]_{HYB}$ for the homopolymer marker regions having low coverage. The hybrid control values $[mean_{CNTL}]_{HYB}$ were used in the MSI score computations described above. The MSI scores for the same samples computed using the hybrid control values show greater uniformity and are distributed over a smaller range of values. The coefficient of variation for the hybrid control, $CV_{HYBRID}$ is 3.7%. These results show that the hybrid control values improved the accuracy of the MSI scores by improving uniformity and reducing variability in results caused by lower coverage and run to run variability.

Information about MSI markers and applications is given in the following publications: R. Bonneville, M. A. Krook et al. Landscape of Microsatellite Instability Across 39 Cancer Types. JCO Precis Oncol. 2017; J. Hempelmann, C. Lockwood et al. Microsatellite instability in prostate cancer by PCR or next-generation sequencing. Journal for Immuno Therapy of Cancer 20186:29; Y. Maruvka, K. Mouw et al. Analysis of somatic microsatellite indels identifies driver events in human tumors, Nature Biotechnology 35, 951-959; and Cortes-Ciriano, S. Lee et al. A molecular portrait of microsatellite instability across multiple cancers, Nature Communications 8, 15180.

According to an exemplary embodiment, there is provided a method for detecting microsatellite instability (MSI) in a sample, including: (1) receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions; (2) for each of the sequence reads, aligning at least a portion the left flank sequence with a reference left flank, wherein the reference left flank borders a reference repeat region of a reference nucleic acid sequence corresponding to the particular marker region; (3) for the repeat region corresponding to a target homopolymer in the sequence reads, calculating a histogram of homopolymer signal values based on flow space signal measurements for the target homopolymer, wherein at least a portion of the marker regions corresponds to target homopolymers; (4) determining a score per marker based on features of the histogram of homopolymer signal values for each marker region corresponding to the target homopolymers to produce a plurality of scores; and (5) combining the plurality of scores to form a total MSI score for the sample. The method may further comprise calculating a histogram of repeat lengths for sequence reads corresponding to the marker region of the target STR, wherein a second portion of the marker regions corresponds to marker regions of target short tandem repeats (STR). The method may further comprise determining a score per STR marker based on features of the histogram of repeat lengths to produce a second plurality of scores. The step of determining a score per STR marker may further comprise calculating a ratio of a second highest number of sequence reads to a first highest number of sequence reads in the histogram of repeat lengths. The method may further comprise applying a sigmoid function to the ratio. The step of combining the plurality of scores may further comprise combining the second plurality of scores with the plurality of scores to form the total MSI score. The step of combining the plurality of scores may further comprise normalizing the total MSI score based on a number of markers meeting a minimum coverage criterion. The method may obtain the total MSI score using a tumor-only analysis. The method may obtain the total MSI score is obtained using a tumor-normal analysis. The step of calculating a histogram of homopolymer signal values may further comprise calculating a sum of M flow space signal measurements corresponding to M nucleotide flows of a sequence of flows having a same nucleotide type as the target homopolymer to form the homopolymer signal value for the sequence read. For sequence reads including sequence reads in a forward direction and sequence reads in a reverse direction, the step of calculating a histogram of homopolymer signal values may further comprise calculating a first histogram of homopolymer signal values for the sequence reads in the forward direction and a second histogram of homopolymer signal values for the sequence reads in the reverse direction. The features may be based on a mean and a standard deviation of the homopolymer signal values. The step of determining a score per marker may further comprise applying a sigmoid function to each of the features. The step of determining a score per marker may further comprise calculating a weighted sum of the features. The step of combining the plurality of scores may further comprise applying a threshold score to the score per marker. The step of combining the plurality of scores may further comprise determining whether the sequence reads associated with the marker region have a coverage level above a minimum coverage level. The step of combining the plurality of scores may further comprise summing the scores of the plurality of scores that meet a threshold criterion and a coverage criterion to form the total MSI score.

According to an exemplary embodiment, there is provided computer-readable media comprising machine-readable instructions that, when loaded in a machine-readable memory and executed by the processor, are configured to cause a system to perform a method detecting microsatellite instability (MSI) in a sample, the method including: (1) receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions; (2) for each of the sequence reads, aligning at least a portion the left flank sequence with a reference left flank, wherein the reference left flank borders a reference repeat region of a reference nucleic acid sequence corresponding to the particular marker region; (3) for the repeat region corresponding to a target homopolymer in the sequence reads, calculating a histogram of homopolymer signal values based on flow space signal measurements for the target homopolymer, wherein at least a portion of the marker regions corresponds to target homopolymers; (4) determining a score per marker based on features of the histogram of homopolymer signal values for each marker region corresponding to the target homopolymers to produce a plurality of scores; and (5) combining the plurality of scores to form a total MSI score for the sample. The method may further comprise calculating a histogram of repeat lengths for sequence reads corresponding to the marker region of the target STR, wherein a second portion of the marker regions corresponds to marker regions of target short tandem repeats (STR). The method may further comprise determining a score per STR marker based on features of the histogram of repeat lengths to produce a second plurality of scores. The step of determining a score per STR marker may further comprise calculating a ratio of a second highest number of sequence reads to a first highest number of sequence reads in the histogram of repeat lengths. The method may further comprise applying a sigmoid function to the ratio. The step of combining the plurality of scores may further comprise combining the second plurality of scores with the plurality of scores to form the total MSI score. The step of combining the plurality of scores may further comprise normalizing the total MSI score based on a number of markers meeting a minimum coverage criterion. The method may obtain the total MSI score using a tumor-only analysis. The method may obtain the total MSI score is obtained using a tumor-normal analysis. The step of calculating a histogram of homopolymer signal values may further comprise calculating a sum of M flow space signal measurements corresponding to M nucleotide flows of a sequence of flows having a same nucleotide type as the target homopolymer to form the homopolymer signal value for the sequence read. For sequence reads including sequence reads in a forward direction and sequence reads in a reverse direction, the step of calculating a histogram of homopolymer signal values may further comprise calculating a first histogram of homopolymer signal values for the sequence reads in the forward direction and a second histogram of homopolymer signal values for the sequence reads in the reverse direction. The features may be based on a mean and a standard deviation of the homopolymer signal values. The step of determining a score per marker may further comprise applying a sigmoid function to each of the features. The step of determining a score per marker may further comprise calculating a weighted sum of the features. The step of combining the plurality of scores may further comprise applying a threshold score to the score per marker. The step of combining the plurality of scores may further comprise determining whether the sequence reads associated with the marker region have a coverage level above a minimum coverage level. The step of combining the plurality of scores may further comprise summing the scores of the plurality of scores that meet a threshold criterion and a coverage criterion to form the total MSI score.

According to an exemplary embodiment, there is provided a system for detecting microsatellite instability (MSI), including a machine-readable memory and a processor configured to execute machine-readable instructions, which, when executed by the processor, cause the system to perform a method for detecting MSI in a sample, the method including: 1) receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions; (2) for each of the sequence reads, aligning at least a portion the left flank sequence with a reference left flank, wherein the reference left flank borders a reference repeat region of a reference nucleic acid sequence corresponding to the particular marker region; (3) for the repeat region corresponding to a target homopolymer in the sequence reads, calculating a histogram of homopolymer signal values based on flow space signal measurements for the target homopolymer, wherein at least a portion of the marker regions corresponds to target homopolymers; (4) determining a score per marker based on features of the histogram of homopolymer signal values for each marker region corresponding to the target homopolymers to produce a plurality of scores; and (5) combining the plurality of scores to form a total MSI score for the sample. The method may further comprise calculating a histogram of repeat lengths for sequence reads corresponding to the marker region of the target STR, wherein a second portion of the marker regions corresponds to marker regions of target short tandem repeats (STR). The method may further comprise determining a score per STR marker based on features of the histogram of repeat lengths to produce a second plurality of scores. The step of determining a score per STR marker may further comprise calculating a ratio of a second highest number of sequence reads to a first highest number of sequence reads in the histogram of repeat lengths. The method may further comprise applying a sigmoid function to the ratio. The step of combining the plurality of scores may further comprise combining the second plurality of scores with the plurality of scores to form the total MSI score. The step of combining the plurality of scores may further comprise normalizing the total MSI score based on a number of markers meeting a minimum coverage criterion. The method may obtain the total MSI score using a tumor-only analysis. The method may obtain the total MSI score is obtained using a tumor-normal analysis. The step of calculating a histogram of homopolymer signal values may further comprise calculating a sum of M flow space signal measurements corresponding to M nucleotide flows of a sequence of flows having a same nucleotide type as the target homopolymer to form the homopolymer signal value for the sequence read. For sequence reads including sequence reads in a forward direction and sequence reads in a reverse direction, the step of calculating a histogram of homopolymer signal values may further comprise calculating a first histogram of homopolymer signal values for the sequence reads in the forward direction and a second histogram of homopolymer signal values for the sequence reads in the reverse direction. The features may be based on a mean and a standard deviation of the homopolymer signal values. The step of determining a score per marker may further comprise applying a sigmoid function to each of the features. The step of determining a score per marker may further comprise calculating a weighted sum of the features. The step of combining the plurality of scores may further comprise applying a threshold score to the score per marker. The step of combining the plurality of scores may further comprise determining whether the sequence reads associated with the marker region have a coverage level above a minimum coverage level. The step of combining the plurality of scores may further comprise summing the scores of the plurality of scores that meet a threshold criterion and a coverage criterion to form the total MSI score.

Figure 12:
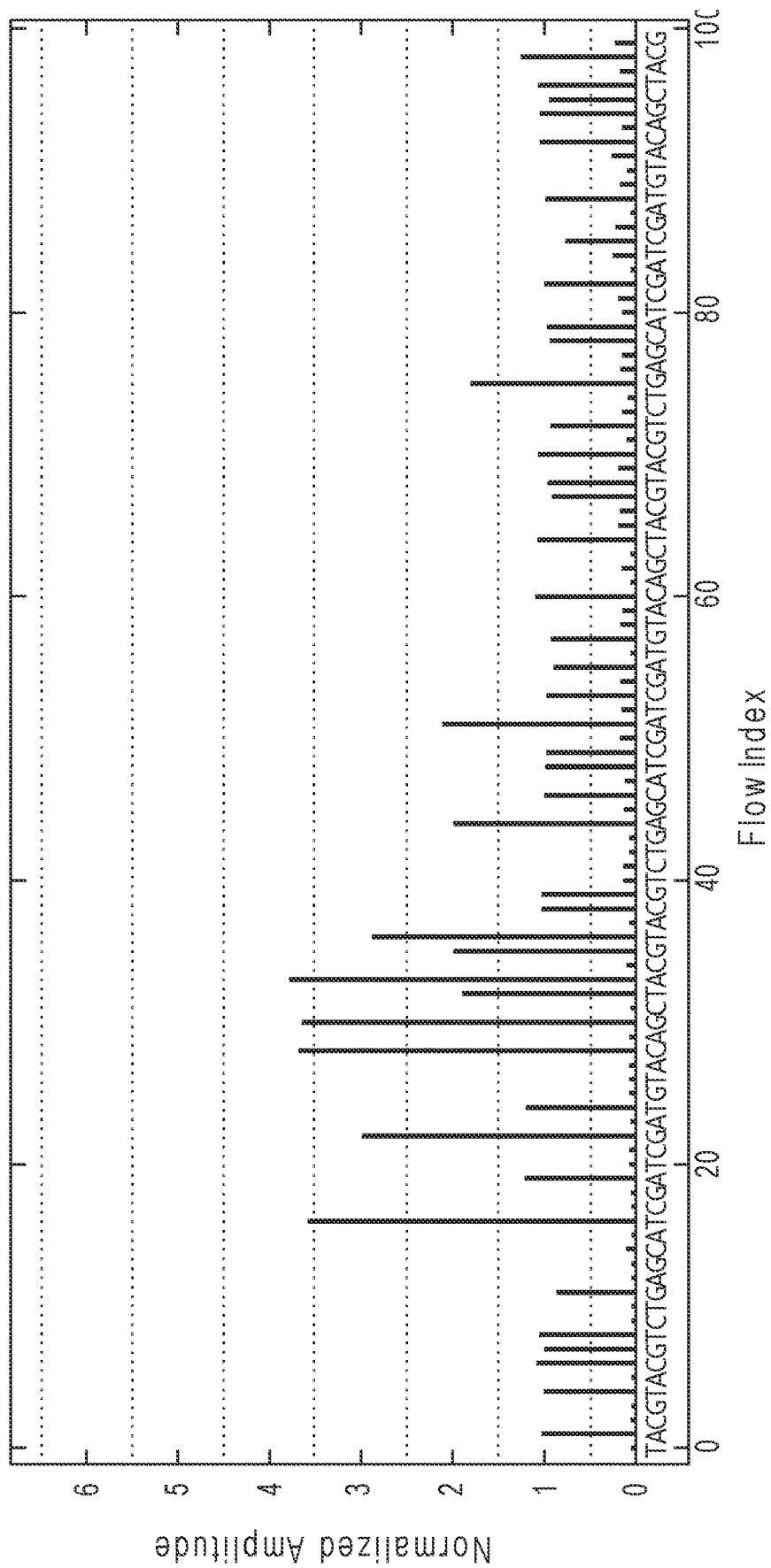
FIG. 12 shows an exemplary representation of flow space signal measurements from which base calls may be made. Figure discloses SEQ ID NO: 3.

FIG. 12 shows an exemplary representation of flow space signal measurements from which base calls may be made. In this example, the x-axis shows the flow number and nucleotide that was flowed in a flow sequence. The bars in the graph show the amplitudes of the flow space signal measurements for each flow from a particular location of a microwell in the sensor array. The numerals on the y-axis show the corresponding number of nucleotide incorporations that may be estimated by rounding to the nearest integer, for example. The number of nucleotide incorporations indicates a homopolymer length. The flow space signal measurements may be raw acquisition data or data having been processed, such as, e.g., by scaling, background filtering, normalization, correction for signal decay, and/or correction for phase errors or effects, etc. The base calls may be made by analyzing any suitable signal characteristics (e.g., signal amplitude or intensity). The structure and/or design of sensor array, signal processing and base calling for use with the present teachings may include one or more features described in U.S. Pat. Appl. Publ. No. 2013/0090860, published Apr. 11, 2013, incorporated by reference herein in its entirety.

For example, the nucleotide flow order is:
ACTGACTGA
and the respective signals generated by a well after each nucleotide flow are:
0.1, 0.3, 0.2, 1.4, 0.3, 1.2, 0.8, 1.5, 0.7
Based on the nucleotide flow sequence, a putative nucleic acid sequence is generated using the signals rounded to the nearest integer (as either a nucleotide incorporation event occurred or did not occur, but not partially). Thus, the above nucleotide flow order and signals establish a putative nucleic acid sequence as follows:

| FLOW SEQUENCE | SIGNAL MEASUREMENT | BASE SEQUENCE |
|---|---|---|
| A | 0.1 | |
| C | 0.3 | |
| T | 0.2 | |
| G | 1.4 | → G |
| A | 0.3 | |
| C | 1.2 | → C |
| T | 0.8 | → T |
| G | 1.5 | → G |
| A | 0.7 | → A |

Once the base sequence for the sequence read is determined, the sequence read may be aligned to a reference sequence to form aligned sequence reads. Methods for forming aligned sequence reads for use with the present teachings may include one or more features described in U.S. Pat. Appl. Publ. No. 2012/0197623, published Aug. 2, 2012, incorporated by reference herein in its entirety. The aligned sequence reads are provided to the processor, for example, in an aligned BAM file.

The BAM file format structure is described in "Sequence Alignment/Map Format Specification," Sep. 12, 2014 (https://github.com/samtools/hts-specs). As described herein, a "BAM file" refers to a file compatible with the BAM format. As described herein, an unaligned BAM file refers to a BAM file that does not contain aligned sequence read information and mapping quality parameters and an aligned BAM file refers to a BAM file that contains aligned sequence read information and mapping quality parameters.

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 13:
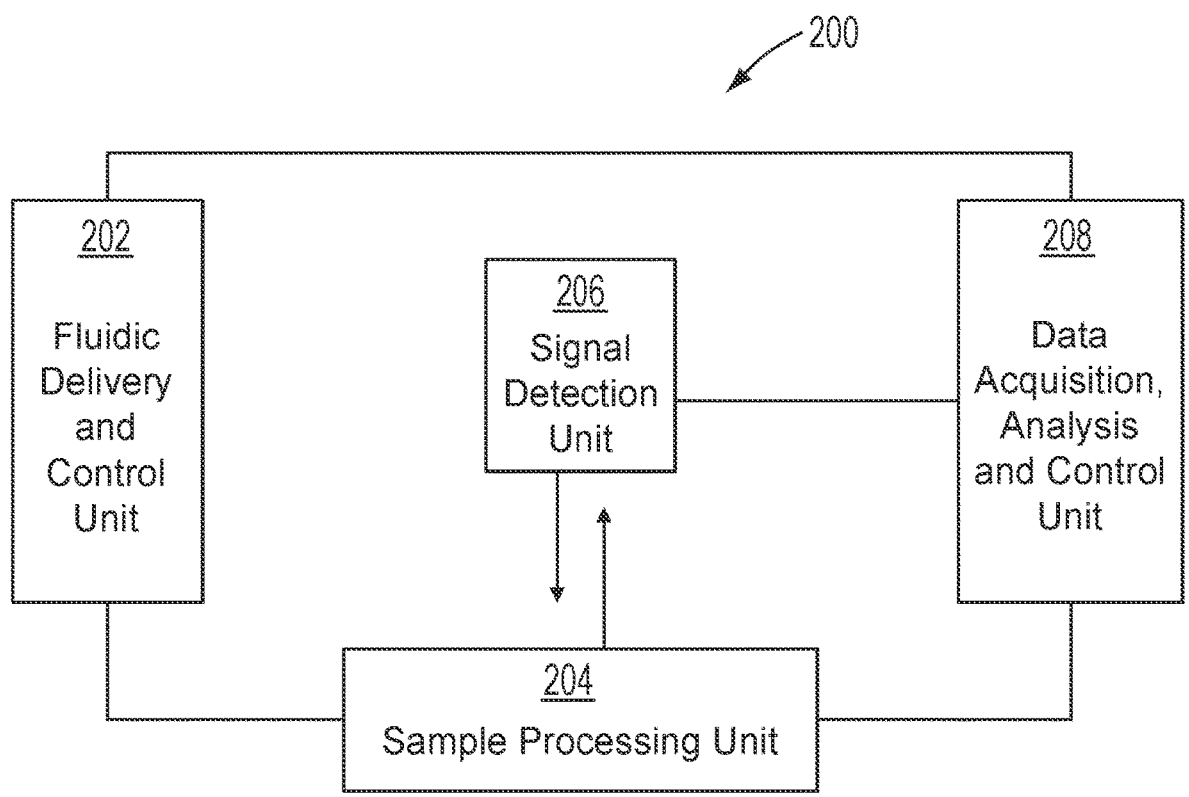
FIG. 13 is a schematic diagram of an exemplary system for a nucleic acid sequencer, in accordance with various embodiments.

Various embodiments of nucleic acid sequencing platforms, such as a nucleic acid sequencer, can include components as displayed in the block diagram of FIG. 13. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R. Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-readable media comprising machine-readable instructions that, when loaded in a machine-readable memory and executed by a processor, are configured to cause a system to perform a method for detecting microsatellite instability (MSI) in a sample, said method comprising:
receiving a plurality of nucleic acid sequence reads corresponding to a plurality of marker regions for MSI, wherein each of the sequence reads includes a left flank sequence, right flank sequence and a repeat region of bases positioned between a rightmost base of the left flank sequence and a leftmost base of the right flank sequence, wherein the repeat region includes a number of repeats of a repeated sequence of bases corresponding to a particular marker region of the plurality of marker regions;
for each sequence read corresponding to the plurality of marker regions for MSI, aligning at least a portion the left flank sequence with a reference left flank, wherein the reference left flank borders a reference repeat region of a reference nucleic acid sequence corresponding to the particular marker region;
for the repeat region corresponding to a target homopolymer in the sequence reads, calculating a histogram of homopolymer signal values based on signal measurements for the target homopolymer, wherein at least a portion of the marker regions corresponds to target homopolymers;
determining a score per marker by calculating a weighted sum of features of the histogram of homopolymer signal values for each marker region corresponding to the target homopolymers to produce a plurality of scores;
applying a threshold score to the score per marker; and
combining the plurality of scores to form a total MSI score for the sample.

2. The computer-readable media of claim 1, wherein the signal measurements comprise flow space signal measurements.

3. The computer-readable media of claim 1, wherein a second portion of the marker regions corresponds to target short tandem repeats (STRs), the method further comprising:
calculating a histogram of repeat lengths for sequence reads corresponding to the marker region of the target STR; and
determining a score per STR marker based on features of the histogram of repeat lengths to produce a second plurality of scores.

4. The computer-readable media of claim 3, wherein the step of determining a score per STR marker further comprises calculating a ratio of a second highest number of sequence reads to a first highest number of sequence reads in the histogram of repeat lengths.

5. The computer-readable media of claim 4, wherein the method further comprises applying a sigmoid function to the ratio.

6. The computer-readable media of claim 3, wherein the step of combining the plurality of scores further comprises combining the second plurality of scores with the plurality of scores to form the total MSI score.

7. The computer-readable media of claim 1, wherein the step of combining the plurality of scores further comprises normalizing the total MSI score based on a number of markers meeting a minimum coverage criterion.

8. The computer-readable media of claim 1, wherein the total MSI score is obtained using a tumor-only analysis.

9. The computer-readable media of claim 1, wherein the total MSI score is obtained using a tumor-normal analysis.

10. The computer-readable media of claim 2, wherein the step of calculating a histogram of homopolymer signal values further comprises calculating a sum of M flow space signal measurements corresponding to M nucleotide flows of a sequence of flows having a same nucleotide type as the target homopolymer to form the homopolymer signal value for the sequence read.

11. The computer-readable media of claim 1, wherein the sequence reads include sequence reads in a forward direction and sequence reads in a reverse direction, wherein the step of calculating a histogram of homopolymer signal values further comprises calculating a first histogram of homopolymer signal values for the sequence reads in the forward direction and a second histogram of homopolymer signal values for the sequence reads in the reverse direction.

12. The computer-readable media of claim 1, further comprising obtaining control homopolymer signal values of sequence reads corresponding to the plurality of marker regions of an on-chip control sample.

13. The computer-readable media of claim 12, further comprising calculating a mean of the control homopolymer signal values and a standard deviation of the control homopolymer signal values corresponding to a given marker.

14. The computer-readable media of claim 13, further comprising calculating a mean of the homopolymer signal values and a standard deviation of the homopolymer signal values corresponding to the given marker of the sample.

15. The computer-readable media of claim 14, further comprising:
for the given marker,
calculating a first difference between the mean of the homopolymer signal values of the sample and the mean of the control homopolymer signal values;
dividing the first difference by the standard deviation of the control homopolymer signal values to form a mean difference; and
calculating a second difference between the standard deviation of the homopolymer signal values of the sample and the standard deviation of the control homopolymer signal values to form a standard deviation difference.

16. The computer-readable media of claim 15, wherein the step of determining a score per marker further comprises, for the given marker, calculating a weighted sum of the mean difference and the standard deviation difference.

17. The computer-readable media of claim 15, wherein the step of determining a score per marker further comprises, for the given marker, applying a first sigmoid function to the mean difference and a second sigmoid function to the standard deviation difference.

18. The computer-readable media of claim 17, wherein the step of determining a score per marker further comprises, for the given marker, calculating a weighted sum of the first sigmoid function of the mean difference and the second sigmoid function of the standard deviation difference.

19. The computer-readable media of claim 1, wherein the step of combining the plurality of scores further comprises determining whether the sequence reads associated with the marker region have a coverage level above a minimum coverage level.

20. The computer-readable media of claim 1, wherein the step of combining the plurality of scores further comprises summing the scores of the plurality of scores that meet a threshold criterion and a coverage criterion to form the total MSI score.

\* \* \* \* \*

```
                            SEQUENCE LISTING

Sequence total quantity: 3
SEQ ID NO: 1            moltype = DNA  length = 19
FEATURE                 Location/Qualifiers
source                  1..19
                        mol_type = other DNA
                        organism = synthetic construct
                        note = synthetic
SEQUENCE: 1
acgtcaaaaa aaaaaggtc                                                    19

SEQ ID NO: 2            moltype = DNA  length = 15
FEATURE                 Location/Qualifiers
source                  1..15
                        mol_type = other DNA
                        organism = synthetic construct
                        note = synthetic
SEQUENCE: 2
acgtcaaaaa aggtc                                                        15

SEQ ID NO: 3            moltype = DNA  length = 100
FEATURE                 Location/Qualifiers
source                  1..100
                        mol_type = other DNA
                        organism = synthetic construct
SEQUENCE: 3
tacgtacgtc tgagcatcga tcgatgtaca gctacgtacg tctgagcatc gatcgatgta    60
cagctacgta cgtctgagca tcgatcgatg tacagctacg                         100
```